(12) United States Patent
Hong et al.

(10) Patent No.: US 11,793,465 B2
(45) Date of Patent: Oct. 24, 2023

(54) DISPLAY DEVICE INCLUDING BIOMETRIC SENSOR AND OPERATING METHOD THEREOF

(71) Applicant: Samsung Display Co., LTD., Yongin-si (KR)

(72) Inventors: Won-Ki Hong, Suwon-si (KR); Hee Seomoon, Hwaseong-si (KR); Hyeon Jun Lee, Seoul (KR)

(73) Assignee: Samsung Display Co., LTD., Yongin-si (KR)

( * ) Notice: Subject to any disclaimer, the term of this patent is extended or adjusted under 35 U.S.C. 154(b) by 342 days.

(21) Appl. No.: 16/953,194

(22) Filed: Nov. 19, 2020

(65) Prior Publication Data

US 2021/0307697 A1    Oct. 7, 2021

(30) Foreign Application Priority Data

Apr. 6, 2020 (KR) .................. 10-2020-0041770

(51) Int. Cl.
*A61B 5/00* (2006.01)
*A61B 5/024* (2006.01)
(Continued)

(52) U.S. Cl.
CPC ........ *A61B 5/6898* (2013.01); *A61B 5/02108* (2013.01); *A61B 5/02427* (2013.01); *A61B 5/6843* (2013.01); *A61B 5/7278* (2013.01); *A61B 5/7445* (2013.01); *A61B 5/7475* (2013.01); *A61B 5/02433* (2013.01);
(Continued)

(58) Field of Classification Search
CPC ... A61B 5/7445; A61B 5/6898; A61B 5/7278; A61B 5/6843; A61B 5/02427; A61B 5/02108; A61B 5/7475; A61B 2562/0247; A61B 5/02433; A61B 2562/0238; H10K 59/60; H10K 59/00; H10K 59/40; H10K 59/12; H10K 50/86; H01L 25/167; G06F 3/041
See application file for complete search history.

(56) References Cited

U.S. PATENT DOCUMENTS 6,475,153 B1 * 11/2002 Khair ................... A61B 5/026
600/485
9,699,544 B2 * 7/2017 Song ..................... H04M 1/724
(Continued)

FOREIGN PATENT DOCUMENTS

JP         2017053728      3/2017
KR    10-2017-0067077      6/2017
(Continued)

*Primary Examiner* — Vinh T Lam
(74) *Attorney, Agent, or Firm* — H.C. Park & Associates, PLC

(57) ABSTRACT

A display device includes: a display panel including a first area having a first light transmissivity and a second area having a second light transmissivity higher than the first light transmissivity; a pressure sensor overlapping the first area; a light emitter overlapping the second area; a light receiver overlapping the second area and spaced from the light emitter; and a processor to control the light emitter and the pressure sensor, and to output a blood pressure signal on a basis of a pressure sensing signal from the pressure sensor and a light sensing signal from the light receiver.

14 Claims, 17 Drawing Sheets

(51) Int. Cl.
  *A61B 5/021* (2006.01)
  *H01L 25/16* (2023.01)
  *G06F 3/041* (2006.01)
  *H10K 59/12* (2023.01)

(52) U.S. Cl.
  CPC .............. *A61B 2562/0238* (2013.01); *A61B 2562/0247* (2013.01); *G06F 3/041* (2013.01); *H01L 25/167* (2013.01); *H10K 59/12* (2023.02)

(56) References Cited

U.S. PATENT DOCUMENTS

| | | | |
|---|---|---|---|
| 9,872,619 B2* | 1/2018 | Lee | A61B 5/0006 |
| 10,206,654 B2 | 2/2019 | Masunishi et al. | |
| 10,265,019 B2* | 4/2019 | Gertsch | A61B 5/0008 |
| 10,466,808 B2* | 11/2019 | Yi | G06F 1/1694 |
| 10,485,431 B1* | 11/2019 | Khachaturian | A61B 5/14542 |
| 10,517,489 B2* | 12/2019 | Narasimhan | A61B 5/11 |
| 10,687,760 B2* | 6/2020 | Lee | A61B 5/02416 |
| 11,154,206 B2* | 10/2021 | Nakazawa | A61B 5/022 |
| 11,172,839 B2* | 11/2021 | Ward | A61B 5/02007 |
| 11,259,712 B2* | 3/2022 | Lee | A61B 5/02433 |
| 11,290,583 B2* | 3/2022 | Hong | A61B 5/0261 |
| 11,317,814 B2* | 5/2022 | Vule | A61B 5/681 |
| 11,357,414 B2* | 6/2022 | Andersen | A61B 5/0295 |
| 11,357,415 B2* | 6/2022 | Siedenburg | A61B 5/02108 |
| 11,508,332 B2* | 11/2022 | Li | G06F 3/041 |
| 11,589,758 B2* | 2/2023 | Pantelopoulos | A61B 5/02125 |
| 11,607,141 B2* | 3/2023 | Yang | A61B 5/6826 |
| 11,612,357 B2* | 3/2023 | Doi | B29C 65/1635 600/499 |
| 2011/0098579 A1* | 4/2011 | Ajiki | A61B 5/02154 600/485 |
| 2014/0275888 A1* | 9/2014 | Wegerich | A61B 5/053 600/324 |
| 2015/0305974 A1* | 10/2015 | Ehrenreich | A61B 5/6833 601/46 |
| 2016/0361031 A1* | 12/2016 | Kim | A61B 5/7445 |
| 2017/0067787 A1 | 3/2017 | Masunishi et al. | |
| 2017/0105633 A1* | 4/2017 | Shin | A61B 5/6802 |
| 2017/0209052 A1* | 7/2017 | Nakamura | A61B 5/0205 |
| 2017/0360306 A1 | 12/2017 | Narasimhan et al. | |
| 2018/0078155 A1* | 3/2018 | Baek | A61B 5/742 |
| 2018/0177413 A1* | 6/2018 | Kwon | A61B 5/6898 |
| 2018/0293420 A1 | 10/2018 | Kim et al. | |
| 2018/0303416 A1* | 10/2018 | Juang | A61B 5/02427 |
| 2019/0231201 A1* | 8/2019 | Kano | A61B 5/7435 |
| 2019/0239758 A1 | 8/2019 | Park et al. | |
| 2019/0246922 A1* | 8/2019 | Matsuo | A61B 5/02438 |
| 2019/0307339 A1 | 10/2019 | Aelen et al. | |
| 2019/0313979 A1 | 10/2019 | Kang et al. | |
| 2019/0380646 A1* | 12/2019 | Gertsch | A41D 1/002 |
| 2020/0022598 A1* | 1/2020 | Matsuura | A61B 5/6843 |
| 2020/0187796 A1* | 6/2020 | Lawrence | A61B 5/7235 |
| 2021/0067618 A1* | 3/2021 | Hong | A61B 5/6898 |
| 2021/0074421 A1* | 3/2021 | Gopalakrishnan | A61B 5/02055 |
| 2021/0296408 A1* | 9/2021 | Hong | H10K 59/60 |
| 2021/0361177 A1* | 11/2021 | Shah | A61B 5/022 |

FOREIGN PATENT DOCUMENTS

| | | |
|---|---|---|
| KR | 10-2018-0114796 | 10/2018 |
| KR | 10-1910518 | 10/2018 |
| KR | 10-2019-0094730 | 8/2019 |
| KR | 10-2019-0119414 | 10/2019 |

* cited by examiner

DISPLAY DEVICE INCLUDING BIOMETRIC SENSOR AND OPERATING METHOD THEREOF

CROSS REFERENCE TO RELATED APPLICATION

This application claims priority from and the benefit of Korean Patent Application No. 10-2020-0041770, filed on Apr. 6, 2020, which is hereby incorporated by reference for all purposes as if fully set forth herein.

BACKGROUND

Field

Exemplary embodiments of the invention relate generally to a display device, and more particularly, to a display device including a biometric sensor and an operating method thereof.

Discussion of the Background

A multi-media electronic device such as a television, a mobile phone, a tablet, a computer, a navigator, a game player, or the like has a display device for displaying a video. The electronic device may be provided with a display device capable of providing a touch-based input scheme which enables a user to easily input information or a command intuitively and conveniently, without a typical input device such as a button, a keyboard, or a mouse. Nowadays, as an individual electronic device such as a mobile phone is widely used, a display device provided with a biometric sensor is increasingly required.

The above information disclosed in this Background section is only for understanding of the background of the inventive concepts, and, therefore, it may contain information that does not constitute prior art.

SUMMARY

Display devices constructed according to the principles and exemplary implementations of the invention include a biometric sensor capable of sensing biometric information having enhanced sensing performance. For example, a display device may sense biometric information of a user, such as blood pressure information, and thus, user convenience may be enhanced. In addition, in some implementations more accurate biometric information may be acquired by correcting the biometric information sensed by the pressure sensor according to the contact area of the pressure sensor.

Additional features of the inventive concepts will be set forth in the description which follows, and in part will be apparent from the description, or may be learned by practice of the inventive concepts.

According to one aspect of the invention, a display device includes: a display panel including a first area having a first light transmissivity and a second area having a second light transmissivity higher than the first light transmissivity; a pressure sensor overlapping the first area; a light emitter overlapping the second area; a light receiver overlapping the second area and spaced from the light emitter; and a processor to control the light emitter and the pressure sensor, and to output a blood pressure signal on a basis of a pressure sensing signal from the pressure sensor and a light sensing signal from the light receiver.

The pressure sensor may include a pressure sensing module including: pressure sensor units; a transmission line to deliver a transmission signal to the pressure sensor units; and receiving lines respectively corresponding to the pressure sensor units, to deliver received signals from the pressure sensor units as the pressure sensing signal.

At least some of the pressure sensor units may include: a first electrode on a base substrate; a second electrode on the base substrate and separated from the first electrode; and a pressure sensing layer directly disposed on the first electrode and the second electrode.

The first electrode may be electrically connected to a corresponding receiving line of the receiving lines, and the second electrode may be electrically connected to the transmission line.

The first electrode may include a first body unit and first branch units to extend from a first unit in a first direction, and the second electrode may include a second body unit and second branch units to extend from a second unit in an opposite direction to the first direction, wherein the first branch units and the second branch units may alternately be disposed in a second direction that intersects with the first direction.

The processor may include: a first analog-to-digital converter to convert the pressure sensing signal to a digital pressure sensing signal; a compensation unit to calculate a contact area on a basis of the digital pressure sensing signal, and to output a pressure-compensated signal in which the digital pressure sensing signal may be compensated according to the contact area; a second analog-to-digital converter to convert the light sensing signal to a digital light sensing signal; and a blood pressure calculation unit to output the blood pressure signal on a basis of the pressure-compensated signal and the digital light sensing signal.

The blood pressure calculation unit may be configured to output a first control signal for the pressure sensor to sense a contact pressure of a user during a blood pressure measurement mode, and to output a second signal for the light emitter to output light. The blood pressure calculation unit may be configured to output, to the display panel, a message for requesting a magnitude of a contact pressure of a user to be gradually increased during a blood pressure measurement mode.

The blood pressure calculation unit may be configured to enter a blood pressure measurement mode, when the contact area is larger than a sensing requirement area.

The compensation unit may be configured to: reduce the digital pressure sensing signal by a prescribed ratio, when the contact area is larger than a first reference value, and increase the digital pressure sensing signal by a prescribed ratio, when the contact area is smaller than a second reference value.

The blood pressure calculation unit may be configured to sense a change in a light sensing level of the digital light sensing signal, while a contact pressure of a user gradually increases and thus a pressure sensing level of the pressure-compensated signal may increase.

The blood pressure calculation unit may be configured to: calculate the pressure sensing level as a mean arterial pressure, which corresponds to a point at which the light sensing level is a maximum, calculate the pressure sensing level of the pressure-compensated signal as a systolic blood pressure, which corresponds to a first ratio of the light sensing level corresponding to the mean arterial pressure, calculate the pressure sensing level as a diastolic blood pressure, which corresponds to a second ratio of the light sensing level corresponding to the mean arterial pressure, and output the blood pressure signal corresponding to each of the systolic blood pressure and the diastolic blood pressure.

The light emitter may include a first light emitting module and a second light emitting module separately disposed from each other.

The pressure sensor may have a shape substantially enclosing at least a portion of the light emitter and the light receiver.

A method of operating a display device having a first area having a first light transmissivity and a second area having a second light transmissivity higher than the first transmissivity, a pressure sensor overlapping the first area, and a light emitter and a light receiver overlapping the second area and spaced from each other, the method including the steps of: sensing a user touch; determining whether a contact area by the user touch is larger than a sensing requirement area; entering a blood pressure measurement mode when the contact area is larger than the sensing requirement area; sensing a contact pressure of a user with the pressure sensor to output a pressure sensing signal; sensing a pulse wave of the user with the light receiver to output a light sensing signal corresponding to the pulse wave; and outputting a blood pressure signal based upon the pressure sensing signal and the light sensing signal.

The step of outputting of the blood pressure signal may include: converting the pressure sensing signal to a digital pressure sensing signal; calculating a contact area based on the digital pressure sensing signal, and outputting a pressure-compensated signal wherein the digital pressure sensing signal may be compensated according to the contact area; converting the light sensing signal to a digital light sensing signal; and outputting the blood pressure signal based on the pressure-compensated signal and the digital light sensing signal.

The step of outputting of the pressure-compensated signal may include: reducing the digital pressure sensing signal by a prescribed ratio, when the contact area is larger than a first reference value; and increasing the digital pressure sensing signal by a prescribed ratio, when the contact area is smaller than a second reference value.

The step of outputting of the blood pressure signal may include: sensing a change in a light sensing level of the digital light sensing signal, while the contact pressure of the user gradually increases and thus as a pressure sensing level of the pressure-compensated signal may increase; calculating the pressure sensing level as a mean arterial pressure, which corresponds to a point at which the light sensing level is a maximum; calculating the pressure sensing level as a systolic blood pressure, which corresponds to a first ratio of the light sensing level corresponding to the mean arterial pressure; calculating the pressure sensing level as a diastolic blood pressure, which corresponds to a second ratio of the light sensing level corresponding to the mean arterial pressure; and outputting the blood pressure signal corresponding to each of the systolic blood pressure and the diastolic blood pressure.

The steps may include outputting a first control signal to activate the pressure sensor to sense the contact pressure of the user, and outputting a second signal to activate the light emitter to output light.

The step may include outputting a message requesting a magnitude of the contact pressure of the user to be gradually increased.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1A:
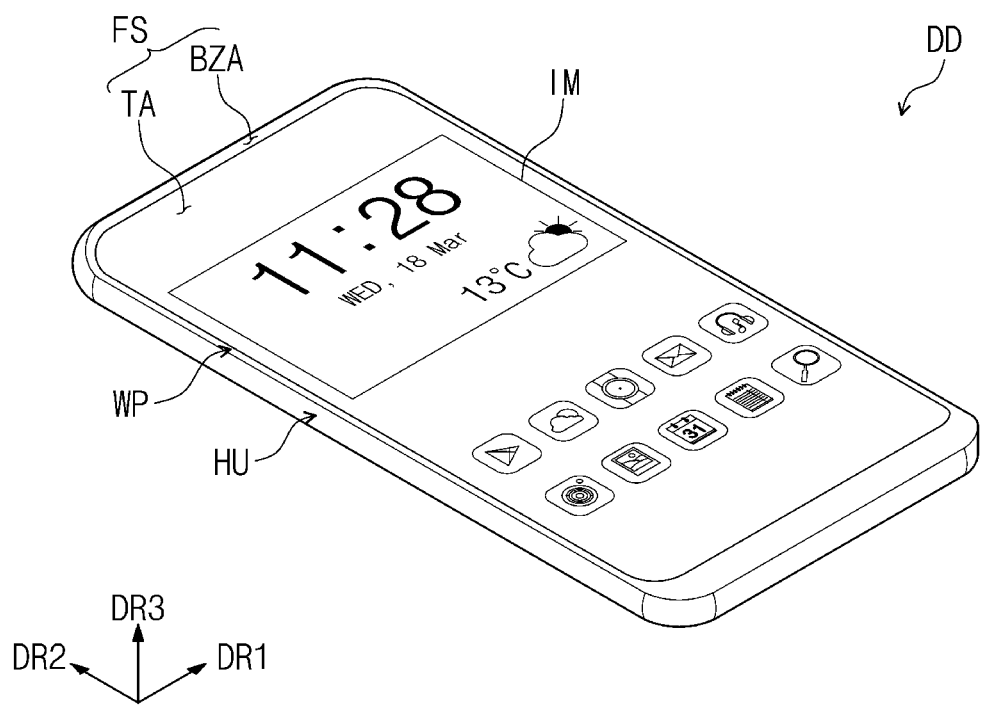
FIG. 1A is a perspective view of an exemplary embodiment of a display device constructed according to principles of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. As an example, when "a component B is being described as directly disposed on a component A" means that there is not a separate adhesive layer/adhesive member between the component A and component B. In that case, component B may be formed through a successive process on the base surface provided by component A, after component A is formed.

To this end, the term "connected" may refer to physical, electrical, and/or fluid connection, with or without intervening elements. Further, the DR1-axis, the DR2-axis, and the DR3-axis are not limited to three axes of a rectangular coordinate system, such as the x, y, and z-axes, and may be interpreted in a broader sense. For example, the DR1-axis, the DR2-axis, and the DR3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "on," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 1B:
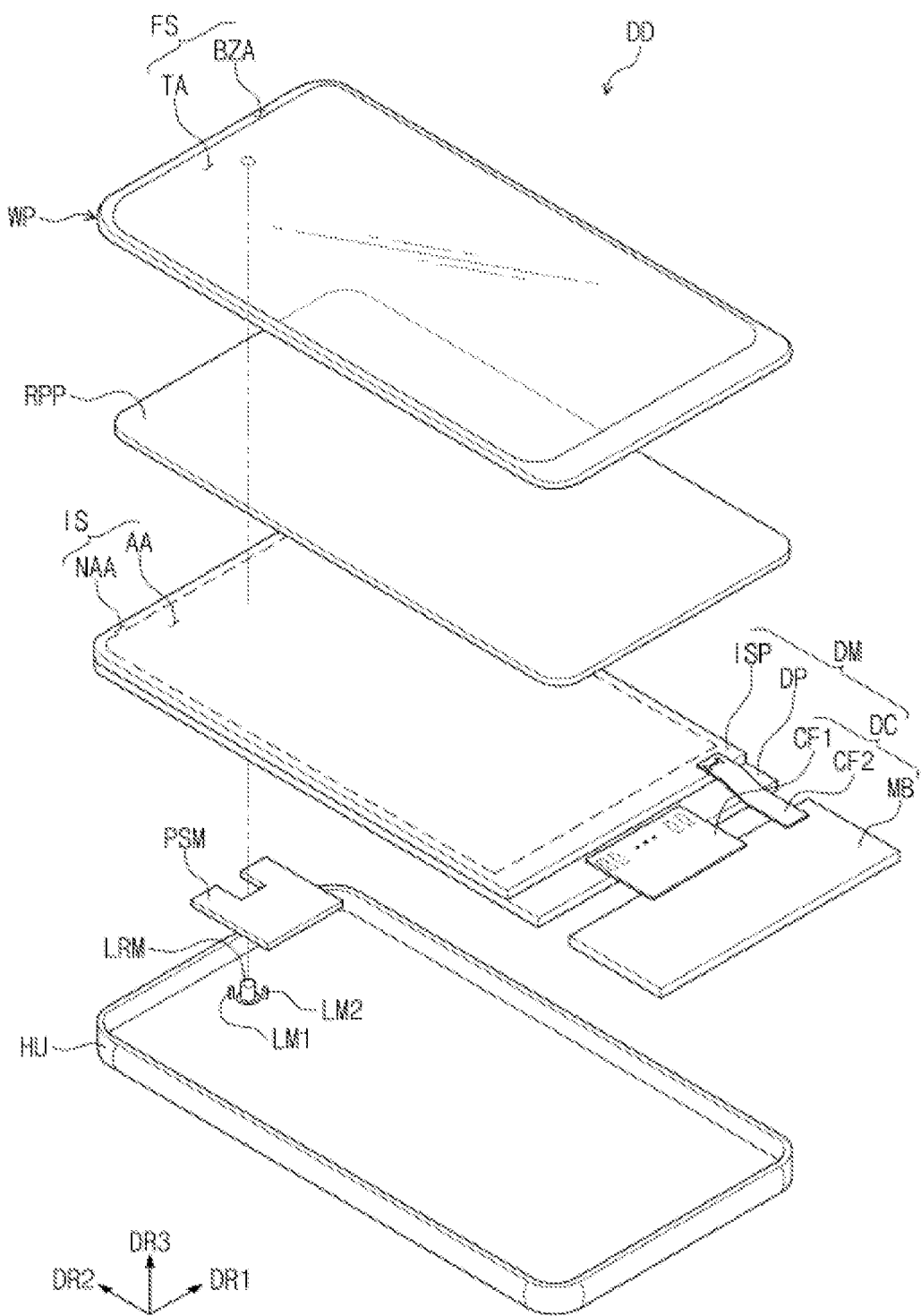
FIG. 1B is an exploded perspective view of the display device of FIG. 1A.

FIG. 1A is a perspective view of an exemplary embodiment of a display device constructed according to principles of the invention. FIG. 1B is an exploded perspective view of the display device of FIG. 1A.

Referring to FIGS. 1A and 1B, the display device DD may be a device activated according to an electrical signal. The display device DD may include various exemplary embodiments. For example, the display device DD may be used in a large electronic device such as a television, a monitor, or an external billboard, or in a small or medium electronic device such as a personal computer, a notebook computer, a personal digital terminal, a car navigation unit, a game console, a portable electronic device, or a camera. In addition, these devices are only enumerated as an exemplary embodiment, and the display device DD may also be employed in or as other electronic devices. In some exemplary embodiments, the display device DD is exemplarily illustrated as a smartphone.

The display device DD may display an image IM on a display surface FS, which is substantially parallel to a first direction DR1 and a second direction DR2, towards a third direction DR3. The image IM may include a still image as well as a moving image. In FIG. 1A, a clock window and application icons are illustrated as an example of the image IM. The display surface FS on which the image IM is displayed may correspond to the front surface of the display device DD and correspond to the front surface of the window panel WP.

In some exemplary embodiments, on the basis of a direction in which the image IM is displayed, a front surface (or an upper surface) and a rear surface (or a lower surface) of each member are defined. The front surface and the rear surface face each other in the third direction DR3, and the normal direction of the front surface and the rear surface may be substantially parallel to the third direction DR3. On the other hand, directions indicated by the first to third directions DR1, DR2, and DR3 are relative concepts to each other and may be changed to other directions.

The display device DD according to some exemplary embodiments may sense a user input applied externally. The user input includes various types of external inputs such as a part of the user's body, light, heat, or pressure. In addition, the display device DD may sense a user input applied to a side surface or the rear surface of the display device DD according to the structure of the display device DD, but the exemplary embodiments are not limited thereto.

The display device DD may include a window panel WP, an anti-reflection panel RPP, a display module DM, a pressure sensor in the form of a pressure sensing module PSM, first and second light emitters in the form of light emitting modules LM1 and LM2, a light receiver in the form of a light receiving module LRM, and a housing HU. In some exemplary embodiments, the window panel WP and the housing HU may be attached to provide the appearance of the display device DD.

The window panel WP may include an optically transparent insulation material. For example, the window panel WP may include a glass or a plastic. The window panel WP may have a multilayer structure or a single-layer structure. For example, the window panel WP may include a plurality of plastic films bonded by an adhesive, or a glass substrate and a plastic film bonded by an adhesive.

The display surface FS of the window panel WP defines the front surface of the display device DD, as described above. The display surface of the display device DD may be divided into a transmission area TA and a bezel area BZA.

The transmission area TA may be an optically transparent area. For example, the transmission area TA may have an area in which optical transmittance is about 90% or more. The bezel area BZA may have a relatively low optical transmittance in comparison to the transmission area TA. The bezel area BZA may have a prescribed color. The bezel area BZA may define the shape of the transmission area TA. The bezel area BZA may be adjacent to the transmission area TA, and surround the transmission area TA. The bezel area BZA may be omitted in the window panel WP according to some exemplary embodiments.

The anti-reflection panel RPP may be disposed under the window panel WP. The anti-reflection panel RPP reduces the reflection ratio of external light input from an upper side of the window panel WP. In some exemplary embodiments, the anti-reflection panel RPP may be omitted, or embedded in the display module DM.

The display module DM may display the image IM and sense an external input. The display module DM includes a front surface IS including an active area AA and a non-active area NAA. The active area AA may be the area activated according to an electrical signal.

In some exemplary embodiments, the active area AA may be the area on which the image IM is displayed, and the external input is sensed. The transmission area TA overlaps at least the active area AA. For example, the transmission area TA overlaps the entire surface of the active area AA or at least a part of the active area AA. Accordingly, a user may visibly recognize the image IM or provide the external input through the transmission area TA. The active area AA may be divided into the area on which the image IM is displayed and the area on which the external input is sensed, but the exemplary embodiments are not limited thereto.

The non-active area NAA may be covered by the bezel area BZA. The non-active area NAA is adjacent to the active area AA. The non-active area NAA may surround the active area AA. In the non-active area NAA, a driving circuit or driving lines for driving the active area AA may be disposed.

In some exemplary embodiments, the display module DM is assembled in a generally flat shape in which the active area AA and the non-active area NAA face the window panel WP. However, this is only exemplary, and a part of the non-active area NAA may be generally curved. In this case, a part of the non-active area NAA faces the rear surface of the display device DD, which results in reduction in the bezel area BZA in the front surface of the display device DD. Alternatively, in the display module DM, a part of the active area AA may also be assembled in a generally curved state.

The display module DM includes a display panel DP, an input sensing panel ISP, and a driving circuit DC. The display panel DP may be a component configured to substantially generate the image IM. The image IM generated by the display panel DP is visibly recognized by the user from the outside through the transmission area TA. The input sensing panel ISP senses an input applied externally. As described above, the input sensing panel ISP may sense an external input provided to the window panel WP.

The driving circuit DC may be electrically connected to the display panel DP and the input sensing panel ISP. The driving circuit DC may include a main circuit board MB, a first circuit board CF1, and a second circuit board CF2.

Each of the first circuit board CF1 and the second circuit board CF2 may be composed of a flexible circuit film. The first circuit board CF1 may provide an electrical signal to the display panel DP, and the second circuit board CF2 may provide an electrical signal for driving the input sensing panel ISP. However, in some exemplary embodiments, the first circuit board CF1 and the second circuit board CF2 may be replaced with a single board. In addition, in some exemplary embodiments, the first circuit board CF1 and the second circuit board CF2 may be omitted, and the main circuit board MB may be directly connected to the display panel DP and the input sensing panel ISP.

The main circuit board MB may include various types of driving circuits for driving the display module DM, or a connector for supplying power, or the like. Each of the first circuit board CF1 and the second circuit board CF2 may be connected to the main circuit board MB. According to some exemplary embodiments, one main circuit board MB may control the display module DM. However, this is only exemplary, and in the display module DM according to some exemplary embodiments, the display panel DP and the input sensing panel ISP may be connected to different main circuit boards, or any one of the first circuit board CF1 and the second circuit board CF2 may not be connected to the main circuit board MB. Accordingly, the exemplary embodiments are not limited to any one specific configuration.

The pressure sensing module PSM, the first and second light emitting modules LM1 and LM2, and the light receiving module LRM may be disposed under the display module DM. In some exemplary embodiments, the pressure sensing module PSM may be attached to the rear surface of the display module DM through an adhesive member.

In a plan view, the pressure sensing module PSM, the first and second light emitting modules LM1 and LM2, and the light receiving module LRM may be disposed overlapping an active area AA. Accordingly, a space in which the pressure sensing module PSM, the first and second light emitting modules LM1 and LM2, and the light receiving module LRM are disposed may be omitted from the bezel area BZA, and an increase in the area of the bezel area BZA may be prevented.

The first and second light emitting modules LM1 and LM2 may output light externally through the transmission area TA, and the light receiving module LRM may receive external light delivered through the transmission area TA. Each of the first and second light emitting modules LM1 and LM2 may be a light source element for outputting light such as an infrared light emitting diode, an organic light emitting diode, a laser diode, or a fluorescent material. Each of the first and second light emitting modules LM1 and LM2 may emit a visible light ray, a near infrared ray (NIR), or a mid-infrared ray (MIR). However, according to the type of a target component desired to be measured or analyzed, the wavelength of the light emitted from the light source element become different. In addition, each light source element is not always composed of a single light emitting body, and may be composed of an array including multiple light emitting bodies. Here, each light source element may emit light of the same wavelength, or emit light of different wavelengths. In FIG. 1B, two light source elements of the first and second light emitting modules LM1 and LM2 are shown, but the number of light emitting modules may be variously changed.

The light receiving module LRM may receive light reflected or scattered by a finger of a user. The light receiving module LRM may be an infrared sensing sensor, a proximity sensor, a charge-coupled device (CCD), a light sensing sensor, a photo transistor, or a photo diode, but is not limited thereto. In some exemplary embodiments, the light receiving module LRM may be a camera. The light receiving module LRM is not always composed of a single element, and may be composed of an array including multiple elements.

The pressure sensing module PSM has a generally U-shape enclosing the first and second light emitting modules LM1 and LM2, and the light receiving module LRM. The shape of the pressure sensing module PSM is not limited to the example shown in FIG. 1B, and may be variously changed. For example, the pressure sensing module PSM has a generally annular shape disposed on the circumference of the first and second light emitting modules LM1 and LM2, and the light receiving module LRM.

The housing HU is attached with the window panel WP. The housing HU may be attached with the window panel WP to provide a space in which the display module DM, the light receiving module LRM, and the first and second light emitting modules LM1 and LM2 are accommodated.

The housing HU may include a material having relatively high hardness. For example, the housing HU may include a plurality of frames and/or plates including a glass, a plastic, a metal, or a combination thereof. The housing HU may stably protect the components of the display device DD accommodated in the internal space from an external impact.

FIGS. 2A to 2D are cross-sectional views of the display device of FIGS. 1A and 1B. FIGS. 2A to 2D illustrate cross sections defined by the first direction DR1 and the third direction DR3. FIGS. 2A to 2D are simply illustrated to explain lamination relationships between functional members forming the display device DD.

The display device DD according to some exemplary embodiments may include a display panel, an input sensor, an anti-reflector, and a window. At least some components among the display panel, the input sensor, the anti-reflector, and the window may be formed in a successive process, or at least some of the components may be attached with each other through an adhesive member. In FIGS. 2A to 2D, an optically clear adhesive OCA is exemplarily illustrated as the adhesive member. The adhesive member to be described below may include a typical adhesive or a pressure sensitive adhesive. The anti-reflector and the window in some exemplary embodiments may be replaced with other components, or omitted.

In FIGS. 2A to 2D, from among the input sensor, the anti-reflector, and the window, a component formed through a successive process with the other components is represented as "a layer". From among the input sensor, the anti-reflector, and the window, a component attached through the adhesive member with the other components is represented as "a panel". The panel includes, for example, a synthetic resin film, a composite material film, a glass substrate, or the like, as a base layer providing a base surface, but the base layer may be omitted from "the layer". In other words, each of the units represented with "layer" is disposed on the base surface provided by another unit.

Hereinbelow, according to the presence/absence of the base layer, the input sensor, the anti-reflector, and the window may be respectively referred to as the input sensing panel ISP, the anti-reflection panel RPP, and the window panel WP, or the input sensing layer ISL, the anti-reflection layer RPL, and the window layer WL.

Figure 2A:
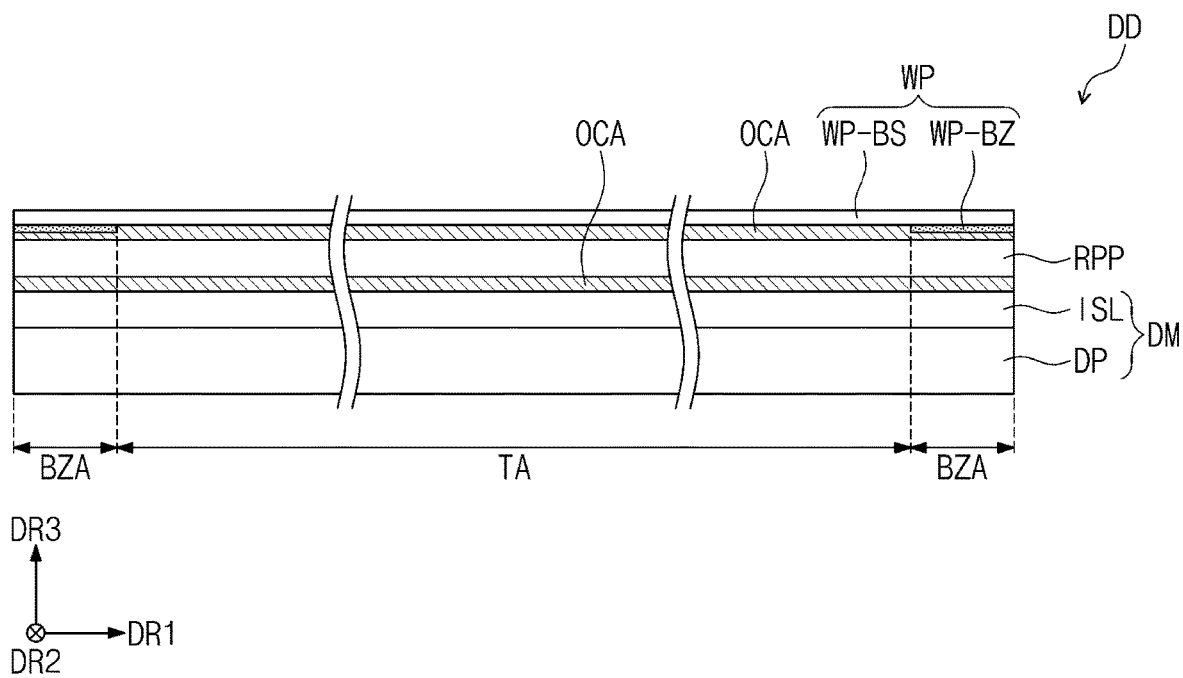
FIGS. 2A to 2D are cross-sectional views of the display device of FIGS. 1A and 1B.

As shown in FIG. 2A, the display device DD may include the display panel DP, the input sensing layer ISL, the anti-reflection panel RPP, and the window panel WP. The input sensing layer ISL may be directly disposed on the display panel DP.

The display panel DP and the input sensing layer ISL directly disposed on the display panel DP may define the display module DM. The optically clear adhesives OCA may be respectively disposed between the display module DM and the anti-reflection panel RPP, and between the anti-reflection panel RPP and the window panel WP.

The display panel DP generates an image, and the input sensing layer ISL acquires coordinate information of an external input (e.g., a touch event). The display module DM according to some exemplary embodiments may further include a protection member disposed on the bottom surface of the display panel DP. The protection member and the display panel DP may be attached through the adhesive member. The display devices DD of FIGS. 2B to 2D to be explained below may also include protection members.

The display panel DP according to some exemplary embodiments may be an emissive display panel, but is not particularly limited thereto. For example, the display panel DP may be an organic light emitting display panel or a quantum dot light emitting display panel, or other known panel. A light emission layer of the organic light emitting display panel includes an organic light emission material. A light emission layer of the quantum dot light emitting display panel may include a quantum dot, a quantum rod, and the like. Hereinafter, the display panel DP is described as the organic light emitting display panel.

The anti-reflection panel RPP reduces a reflection ratio of the external light input from the upper side of the window panel WP. The anti-reflection panel RPP according to some exemplary embodiments may include a phase retarder and a polarizer. The phase retarder may be a film type or a liquid crystal coating type, and include a λ/2 phase retarder and/or a λ/4 phase retarder. The polarizer may also be a film type, and include a stretchable synthetic resin film. The phase retarder and the polarizer may further include protection films. The phase retarder and the polarizer themselves or the protection film may be defined as the base layer of the anti-reflection panel RPP.

The anti-reflection panel RPP according to some exemplary embodiments may include color filters. The color filters have a prescribed array. The array of the color filters may be determined in consideration of light emission colors of pixels included in the display panel DP. The anti-reflection panel RPP may further include a black matrix adjacent to the color filters.

The anti-reflection panel RPP according to some exemplary embodiments may include a destructive interference structure. For example, the destructive interference structure may include a first reflection layer and a second reflection layer disposed on different layers. First reflection light and second reflection light respectively reflected by the first reflection layer and the second reflection layer may be destructively interfered, and thus an external light reflection ratio is reduced.

The window panel WP according to some exemplary embodiments includes a base layer WP-BS and a light shield pattern WP-BZ. The base layer WP-BS may include a glass substrate and/or a synthetic resin film. The base layer WP-BS is not limited to a single layer. The base layer WP-BS may include two or more films that are attached through the adhesive member.

The light shield pattern WP-BZ partially overlaps the base layer WP-BS. The light shield pattern WP-BZ is disposed on the rear surface of the base layer WP-BS, and the light shield pattern WP-BZ may substantially define the bezel area BZA of the display device DD. The area on which the light shield pattern WP-BZ is not disposed may define the transmission area TA of the display device DD. In restriction to the window WP, the area on which the light shield pattern WP-BZ is disposed is defined as a light shield area of the window panel WP, and the area on which the light shield pattern WP-BZ is not disposed is defined as a transmission area of the window panel WP.

Figure 2B:
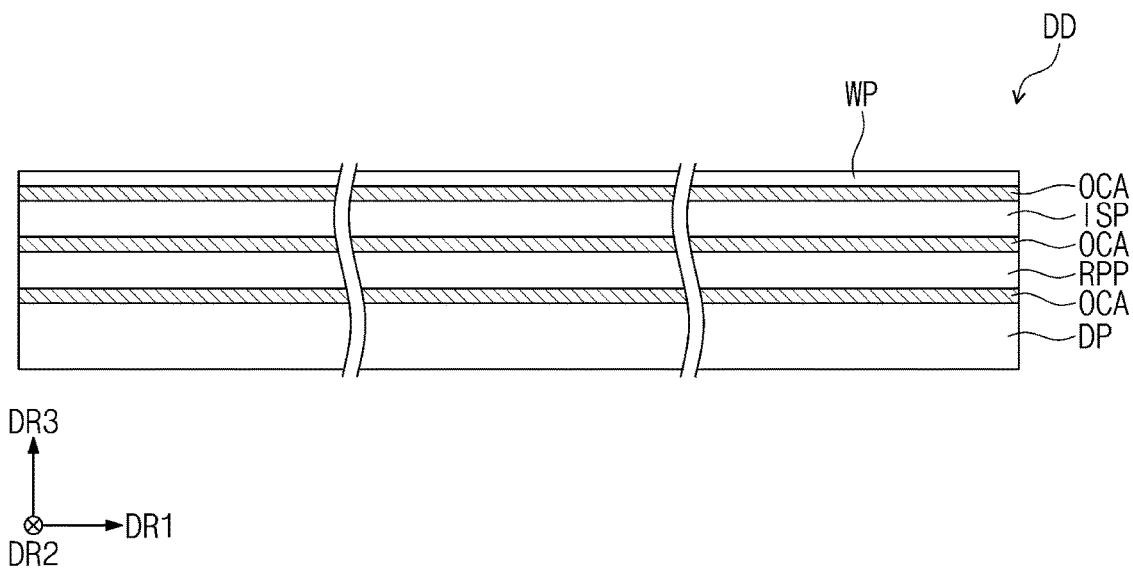
Figure 2C:
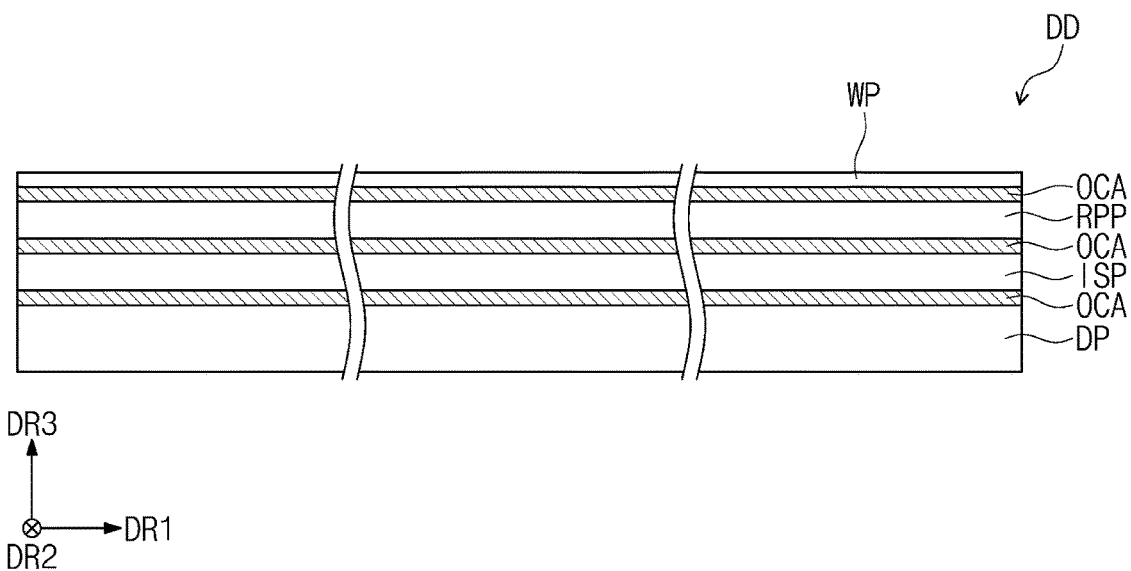
Figure 2D:
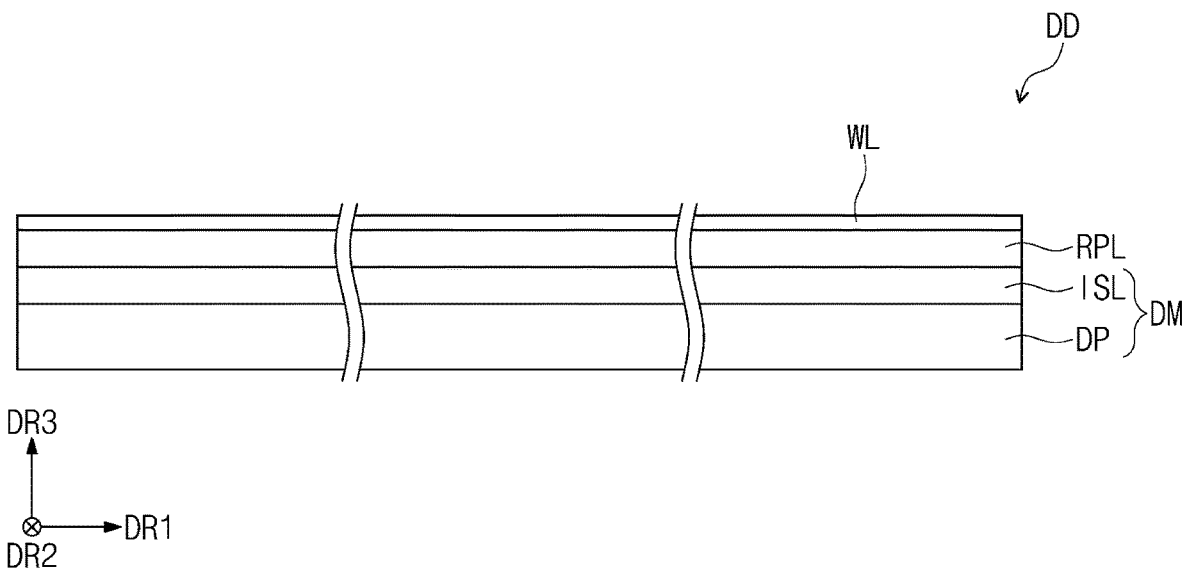

The light shield pattern WP-BZ may have a multilayer structure. The multilayer structure may include a color layer of a chromatic color and a light shield layer of black color. The color layer of a chromatic color and the light shield layer of black color may be formed through deposition, printing, and coating processes. The window panel WP may further include a functional coating layer disposed on the front surface of the base layer WP-BS. The functional coating layer may include a fingerprint prevention layer, an anti-reflection layer, and a hard coating layer, etc. In FIGS. 2B to 2D, the window panel WP is simply illustrated without distinction between the base layer WP-BS and the light shield pattern WP-BZ.

As shown in FIGS. 2B and 2C, the display device DD may include the display panel DP, the input sensing panel ISP, the anti-reflection panel RPP, and the window panel WP. The lamination order of the input sensing layer ISL and the anti-reflection panel RPP may be changed.

As shown in FIG. 2D, the display device DD may include the display panel DP, the input sensing layer ISL, the anti-reflection layer RPL, and the window layer WL. In contrast to the display device DD shown in FIG. 2A, the optically clear adhesives are omitted, and the input sensing layer ISL, the anti-reflection layer RPL, and the window layer WL are formed in a successive process on the base surface provided on the display panel DP. The lamination order of the input sensing layer ISL and the reflection prevention layer RPL may be changed.

Figure 3:
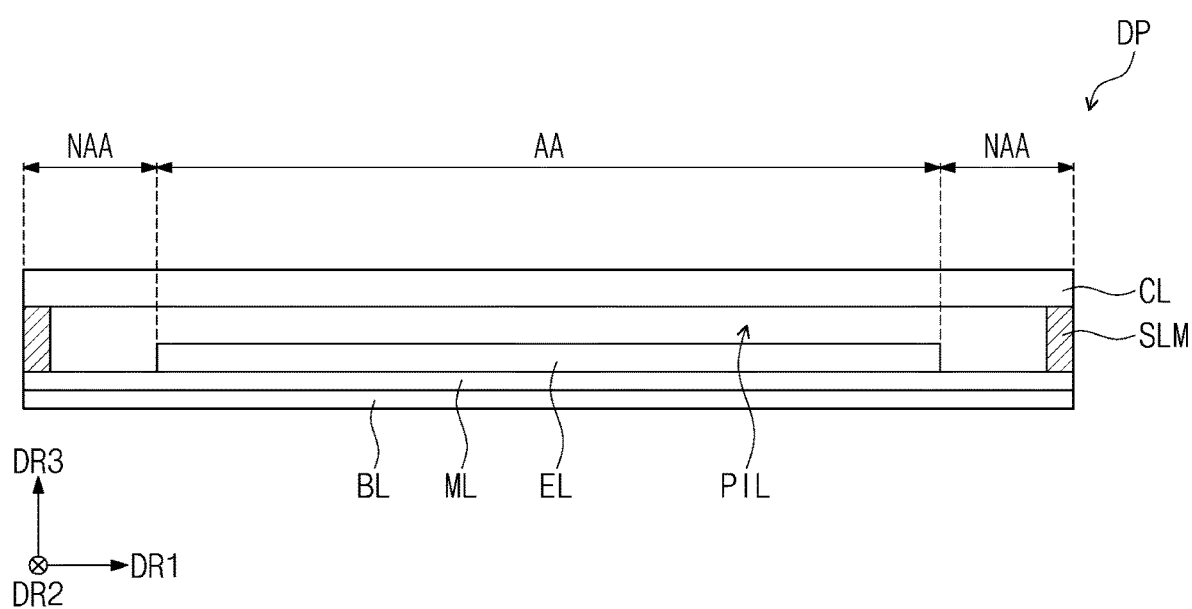
FIG. 3 is a cross-sectional view of an exemplary embodiment of a display panel constructed according to principles of the invention that may be used in the display device of FIGS. 1A and 1B.

FIG. 3 is a cross-sectional view of an exemplary embodiment of a display panel constructed according to principles of the invention that may be used in the display device of FIGS. 1A and 1B.

With reference to FIG. 3, the display panel DP may include a base layer BL, a circuit layer ML, a light emitting element layer EL, an encapsulation layer CL, and a combination member SLM. Each of the base layer BL and the encapsulation layer CL may have a silicon substrate, a plastic substrate, a glass substrate, an insulation film, or a laminate structure including a plurality of insulation layers. The circuit layer ML may be disposed on the base layer BL. The circuit layer ML may include a plurality of insulation layers, a plurality of conductive layers, and a semiconductor layer. The plurality of conductive layers of the circuit layer ML may provide signal wirings or a control circuit of pixels.

The light emitting element layer EL may be disposed on the circuit layer ML. The light emitting element layer EL may be a layer for generating light. For example, the light emitting element layer EL may include organic light emitting diodes. However, the exemplary embodiments are not limited thereto, and the light emitting element layer EL may also include inorganic light emitting diodes, or organic-inorganic light emitting diodes. The encapsulation layer CL may be disposed on the light emitting element layer EL. A prescribed space PIL may be defined between the encapsulation layer CL and the light emitting element layer EL. The space PIL may be filled with air or an inert gas.

A combination member SLM may be disposed between the base layer BL and the encapsulation layer CL. The combination member SLM may connect together the base layer BL and the encapsulation layer CL. The combination member SLM may include an organic material such as a photo-curable resin or a photo-plastic resin, or an inorganic material such as a frit seal, but the exemplary embodiments are not limited thereto.

Figure 4:
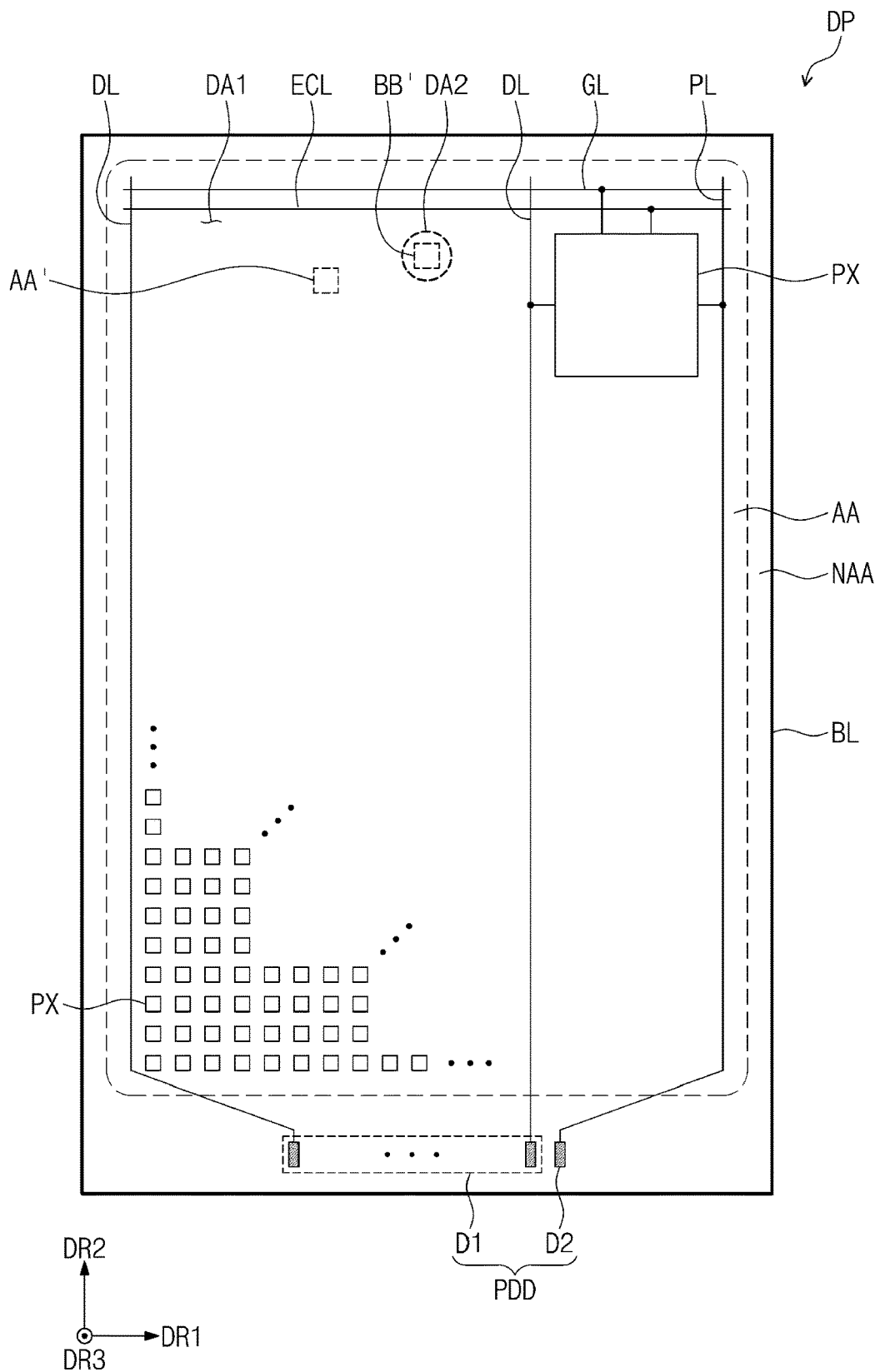
FIG. 4 is a plan view of the display panel of FIG. 3.

FIG. 4 is a plan view of the display panel of FIG. 3. With reference to FIG. 4, the display panel DP may include the base layer BL, a plurality of pixels PX, a plurality of signal lines GL, DL, PL, and ECL, and a plurality of display pads PDD.

In FIG. 4, the active area AA and the non-active area NAA of the display panel DP are illustrated. The active area AA of the display panel DP is the area on which an image is displayed, and the non-active area NAA may be the area in which a driving circuit, a driving wiring, or the like is disposed. The plurality of pixels PX may be disposed in the active area AA.

A first area DA1 and a second area DA2 may be defined in the display panel DP. The first area DA1 and the second area DA2 may compose the active area AA of the display panel DP. The first area DA1 may surround the second area DA2.

The second area DA2 may be the area overlapping the light receiving module LRM (see FIG. 1B) the first light emitting module LM1 (see FIG. 1B) and the second light emitting module LM2 (see FIG. 1B) in a plan view. The first area DA1 may have different resolution from the second area DA2. For example, the resolution of the second area DA2 may be lower than that of the first area DA1 because it contains less pixels.

The second area DA2 may have higher transmissivity than the first area DA1. Accordingly, it may be easy to transmit/receive an optical signal to/from the light receiving module LRM, the first light emitting module LM1, and the second light emitting module LM2 disposed in the second area DA2.

The plurality of signal lines GL, DL, PL, and ECL are connected to the pixels PX to transfer electrical signals to the pixels PX. Among the signal lines included in the display panel DP, a scan line GL, a data line DL, a power line PL, and a light emission control line ECL are exemplarily illustrated. However, these are exemplary, and the signal lines GL, DL, PL, and ECL may further include an initialization voltage line. The exemplary embodiments are not limited thereto.

The display pads PDD may include a first pad D1 and a second pad D2. The first pad D1 may be provided in plurality to be respectively connected to the data lines DL. The second pad D2 may be electrically connected to the power line PL. The display panel DP may provide, to the pixels PX, electrical signals externally provided through the display pads PDD. On the other hand, the display pads PDD may further include pads for receiving other electrical signals besides the first pad D1 and the second pad D2, and the exemplary embodiments are not limited thereto.

Figure 5:
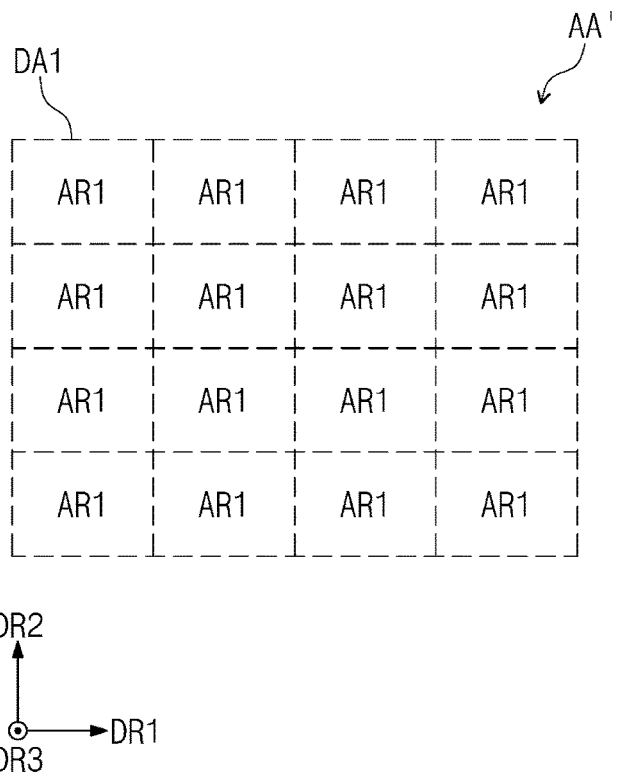
FIG. 5 is an enlarged plan view of area AA' of FIG. 4.

FIG. 5 is an enlarged plan view of area AA' of FIG. 4.

With reference to FIGS. 4 and 5, the first area DA1 may be divided into first sub-areas AR1. At least one representative pixel may be disposed in each of the first sub-areas AR1. The first sub-areas AR1 may be arranged along the first direction DR1 and the second direction DR2. The pixels disposed in the first sub-areas AR1 may provide light.

Figure 6:
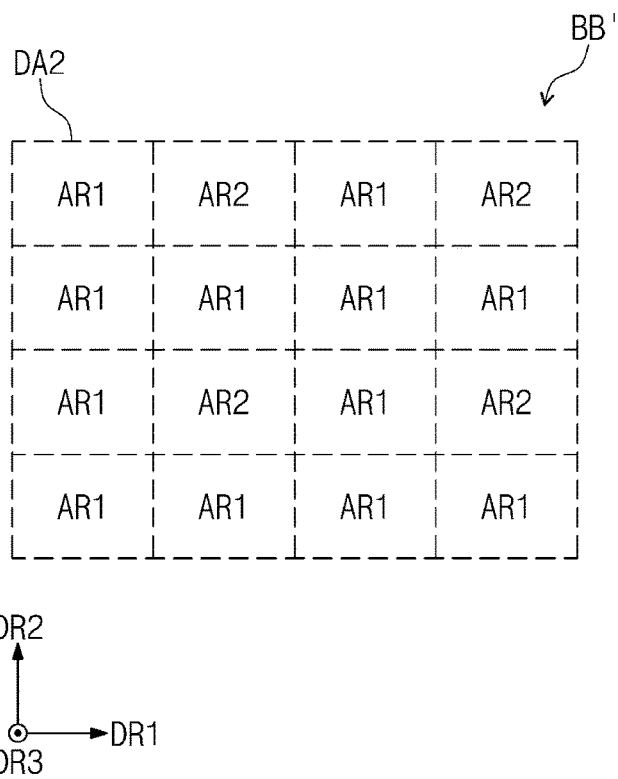
FIG. 6 is an enlarged plan view of area BB' of FIG. 4.

FIG. 6 is an enlarged plan view of area BB' of FIG. 4.

With reference to FIGS. 4 and 6, the second area DA2 may include a first sub-area AR1 and a second sub-area AR2. The first sub-area AR1 may be substantially the same as one of the first sub-areas AR1 of FIG. 5. The second sub-area AR2 may include less pixels than the number of pixels in the first sub-area AR1. For example, at least one pixel is disposed in the first sub-area AR1, and at least one pixel is missing from the second sub-area AR2. The missing pixel may be a representative pixel in which some of components defining the pixel is missing. The pixel disposed in the first sub-area AR1 may provide light. The missing pixel disposed in the second sub-area AR2 may not provide light. In other words, in some exemplary embodiments, the second sub-area AR2 may not include a pixel. The second sub-area AR2 may be referred to as a low reflection area, a transmission area, a non-display area, a non-light emission area, a transflective area, or the like. The second area DA2 includes the second sub-area AR2 that does not provide an image, and thus may have a lower resolution than the first area DA1.

The first sub-area AR1 may be provided in plural (hereinafter, first sub-areas) and the second sub-area AR2 may be provided in plural (hereinafter, second sub-areas). The first sub-areas AR1 and the second sub-areas AR2 may be arrayed according to a prescribed rule. With reference to FIG. 6, the first sub-areas AR1 and the second sub-areas AR2 may be alternately arrayed along the first direction DR1 in a first row. In a second row, the first sub-areas AR1 may be arrayed along the first direction DR1. The first row and the second row may be alternately arrayed along the second direction DR2.

In FIG. 6, the relative position between the first sub-areas AR1 and the second sub-areas AR2 is exemplarily illustrated. However, the exemplary embodiments are not limited thereto. When the second area DA2 includes both the first sub-areas AR1 and the second sub-areas AR2, configuration of the sub-areas may be changed in various ways.

Figure 7:
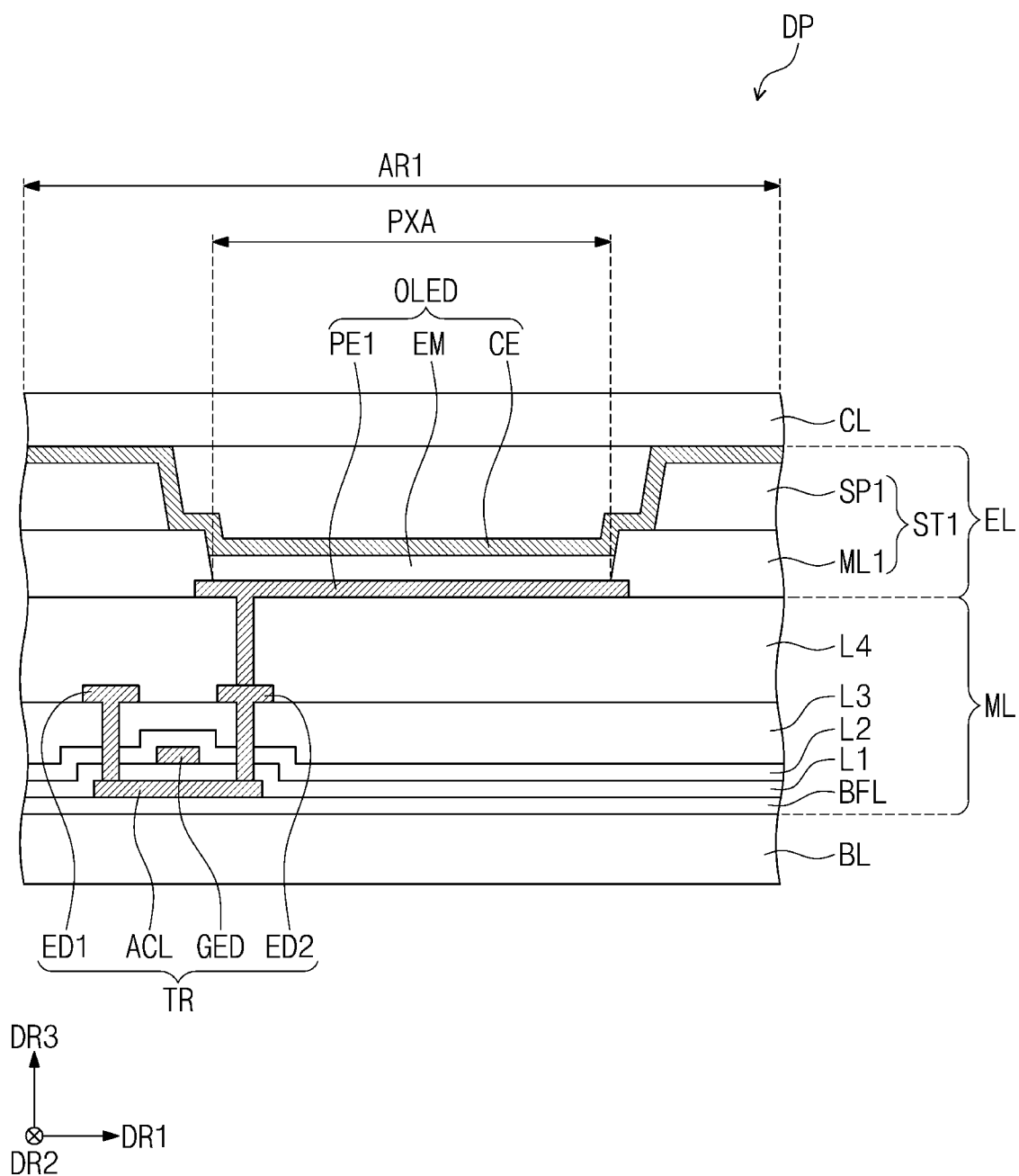
FIG. 7 is a cross-sectional view illustrating an exemplary embodiment of a part of the display panel constructed according to principles of the invention.

FIG. 7 is a cross-sectional view illustrating an exemplary embodiment of a part of the display panel constructed according to principles of the invention. The area illustrated in FIG. 7 may be the first sub-area AR1. The first sub-area AR1 may be the area included in the first area DA1 (see FIG. 4). In addition, the first sub-area AR1 may be the area included in the second area DA2 (see FIG. 4).

With reference to FIGS. 4 and 7, each representative pixel PX may include a light emitting element OLED and a pixel circuit. The pixel circuit may include at least one transistor TR. The pixel circuit may further include a capacitor. In each pixel PX, a pixel area may be defined, and in FIG. 7, one representative pixel area PXA is shown.

The display panel DP may include a base layer BL, a circuit layer ML, a light emitting element layer EL, and an encapsulation layer CL. The circuit layer ML may include a transistor TR and a plurality of insulation layers BFL, L1, L2, L3, and L4. An insulation layer BFL may be disposed on the base layer BL, and the transistor TR may be disposed on the insulation layer BFL. The transistor TR may include a semiconductor layer ACL, a control electrode GED, a first electrode ED1 and a second electrode ED2.

The semiconductor layer ACL may be disposed on the insulation layer BFL. The insulation layer BFL may be a buffer layer for providing a low surface energy to the semiconductor layer ACL. In this case, the semiconductor layer ACL may have higher adhesion for the insulation layer BFL than the base layer BL. In addition, the insulation layer BFL may be a barrier layer for protecting the bottom surface of the semiconductor layer ACL. In this case, the insulation layer BFL may cut off contamination, moisture, or the like flowed in from the base layer BL itself, or through the base layer BL from being permeated into the semiconductor layer ACL. In addition, the insulation layer BFL may be a light barrier layer for blocking external light incident through the base layer BL from being incident to the semiconductor layer ACL. In this case, the insulation layer BFL may further include a light barrier material.

The semiconductor layer ACL may include a polysilicon or an amorphous silicon. Besides, the semiconductor layer ACL may include a metal-oxide semiconductor. The semiconductor layer ACL may include a channel area for playing a role of a path through which an electron or hole can move, and a first ion-doped area and a second ion-doped area disposed with the channel area therebetween.

The first insulation layer L1 may be disposed on the insulation layer BFL, and cover the semiconductor layer ACL. The first insulation layer L1 may include an inorganic material. The inorganic material may include at least any one among a silicon nitride, a silicon oxynitride, a silicon oxide, a titanium oxide, or an aluminum oxide. The control electrode GED may be disposed on a first insulation layer L1. A second insulation layer L2 may be disposed on the first insulation layer L1 and cover the control electrode GED. The second insulation layer L2 may include an inorganic material.

A third insulation layer L3 may be disposed on the second insulation layer L2. The first electrode ED1 and the second electrode ED2 may be disposed on the third insulation layer L3. Each of the first electrode ED1 and the second electrode ED2 may be connected to the semiconductor layer ACL through through-holes penetrating the first insulation layer L1, the second insulation layer L2, and the third insulation layer L3. In some exemplary embodiments, the first electrode ED1 may be connected to the first ion-doped area, which is one side of the semiconductor layer ACL, and to the second ion-doped area that is the other side of the semiconductor layer ACL.

The fourth insulation layer L4 may be disposed on the third insulation layer L3, and cover the first electrode ED1 and the second electrode ED2. The fourth insulation layer L4 may be formed of a single layer or a plurality of layers. For example, the single layer may include an organic layer. The plurality of layers may be provided with an organic layer and an inorganic layer that are laminated. The fourth insulation layer L4 may be a planarization layer for providing a planar surface.

The light emitting element layer EL may be disposed on the fourth insulation layer L4. The light emitting element layer EL may include a light emitting element OLED and a first laminate structure ST1. The light emitting element OELD may include a first pixel electrode PE1, an emission layer EM, and a common electrode CE. The first pixel electrode PE1 may be disposed on the fourth insulation layer L4, and be electrically connected to the second electrode ED2 through a through-hole defined in the fourth insulation layer L4. In addition, the first pixel electrode PE1 may be disposed in the pixel area PXA.

The emission layer EM may be disposed on the first pixel electrode PE1. The emission layer EM may have a single layer structure formed from a single material, a single layer structure formed from a plurality of different materials, or a multilayer structure having a plurality of layers formed from a plurality of different materials. The emission layer EM may include an organic material. The organic material is a typically used material and is not particularly limited. For example, the emission layer EM may include at least any one among materials emitting a red, a green, or a blue color light, and may include a fluorescent material or a phosphorescent material.

The first laminate structure ST1 may be disposed adjacent to the first pixel electrode PE1. The first laminate structure ST1 may include a first intermediate layer ML1 and a first spacer SP1. The first intermediate layer ML1 may be disposed on the circuit layer ML to define the pixel area PXA. The first intermediate layer ML1 may expose at least a portion of the first pixel electrode PE1 and be disposed on the fourth insulation layer L4. The portion of the first pixel electrode PE1 may not be covered with the first intermediate layer ML1, but may correspond to the pixel area PXA. The first intermediate layer ML1 may be referred to as a pixel definition layer. A first spacer SP1 may be disposed on the first intermediate layer ML1. The area of the first spacer SP1 may be smaller than that of the first intermediate layer ML1 in a plan view. Accordingly, a portion of the top surface of the first intermediate layer ML1 may be exposed by the first spacer SP1. The first spacer SP1 may play a role in supporting the encapsulation layer CL.

The common electrode CE may be disposed on the emission layer EM and the first laminate structure ST1. The common electrode CE may be disposed on a side surface and an exposed top surface of the first intermediate layer ML1, and on a side surface and the top surface of the first spacer SP1. In some exemplary embodiments, a protection layer covering the common electrode CE may be further disposed. The protection layer may include an inorganic material, and protect the common electrode CE from being oxidized.

Figure 8:
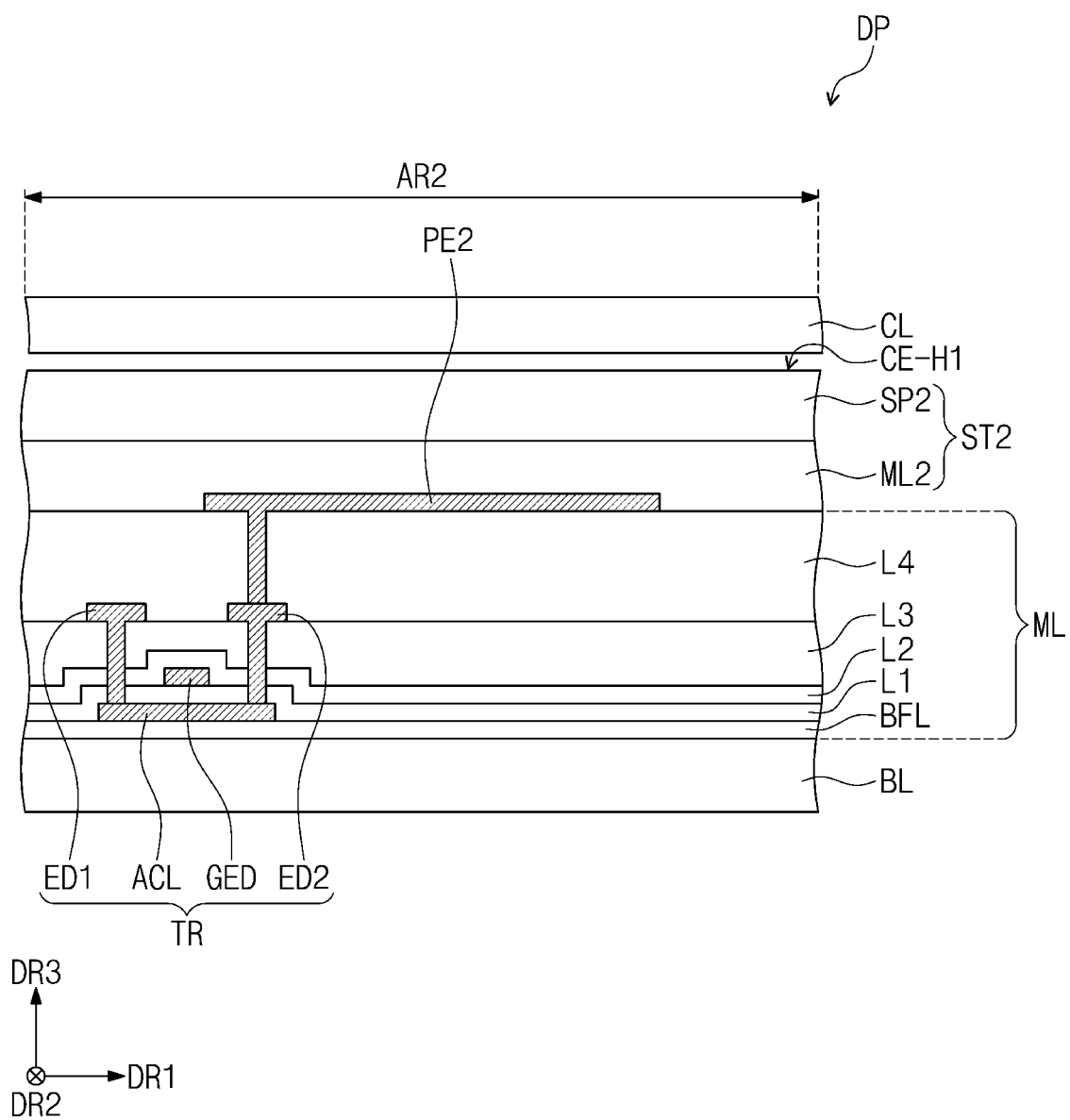
FIG. 8 is a cross-sectional view illustrating an exemplary embodiment of another part of the display panel constructed according to principles of the invention.

FIG. 8 is a cross-sectional view illustrating an exemplary embodiment of another part of the display panel constructed according to principles of the invention. The area illustrated in FIG. 8 may be the second sub-area AR2. The second sub-area AR2 may be the area included in the second area DA2 (see FIG. 4). The second sub-area AR2 may be the area from which light is not provided.

With reference to FIG. 8, the second pixel electrode PE2 may be disposed in the second sub-area AR2. The second laminate structure ST2 may be disposed adjacent to the second pixel electrode PE2. The second laminate structure ST2 may have a different shape from the first laminate structure ST1 (see FIG. 7). For example, the second laminate structure ST2 may include a second intermediate layer ML2 and a second spacer SP2. The second intermediate layer ML2 may completely cover the second pixel electrode PE2. The area of the second intermediate layer ML2 may be substantially the same as that of the second spacer SP2 in the second sub-area AR2. Accordingly, the top surface of the second intermediate layer ML2 may be fully covered with the second spacer SP2.

The second intermediate layer ML2 may include the same material as the first intermediate layer ML1 (see FIG. 7), and be formed through the same process. The second spacer SP2 may include the same material as the first spacer SP1 (see FIG. 7), and be formed through the same process. A common electrode CE is not disposed in the second sub-area AR2. For example, a hole CE-H1 may be provided in the common electrode CE. Since the common electrode CE is not disposed in the second sub-area AR2, the second sub-area AR2 may have a higher transmissivity than the first sub-area AR1 (see FIG. 7).

As is clear from FIGS. 4, 5, and 6, the first area DA1 only includes the first sub-area AR1, and the second area DA2 includes the first sub-area AR1 and the second sub-area AR2. Accordingly, the second area DA2, which includes the second sub-area AR2 in which the common electrode is not disposed, may have a higher light transmissivity than the first area DA1.

Figure 9A:
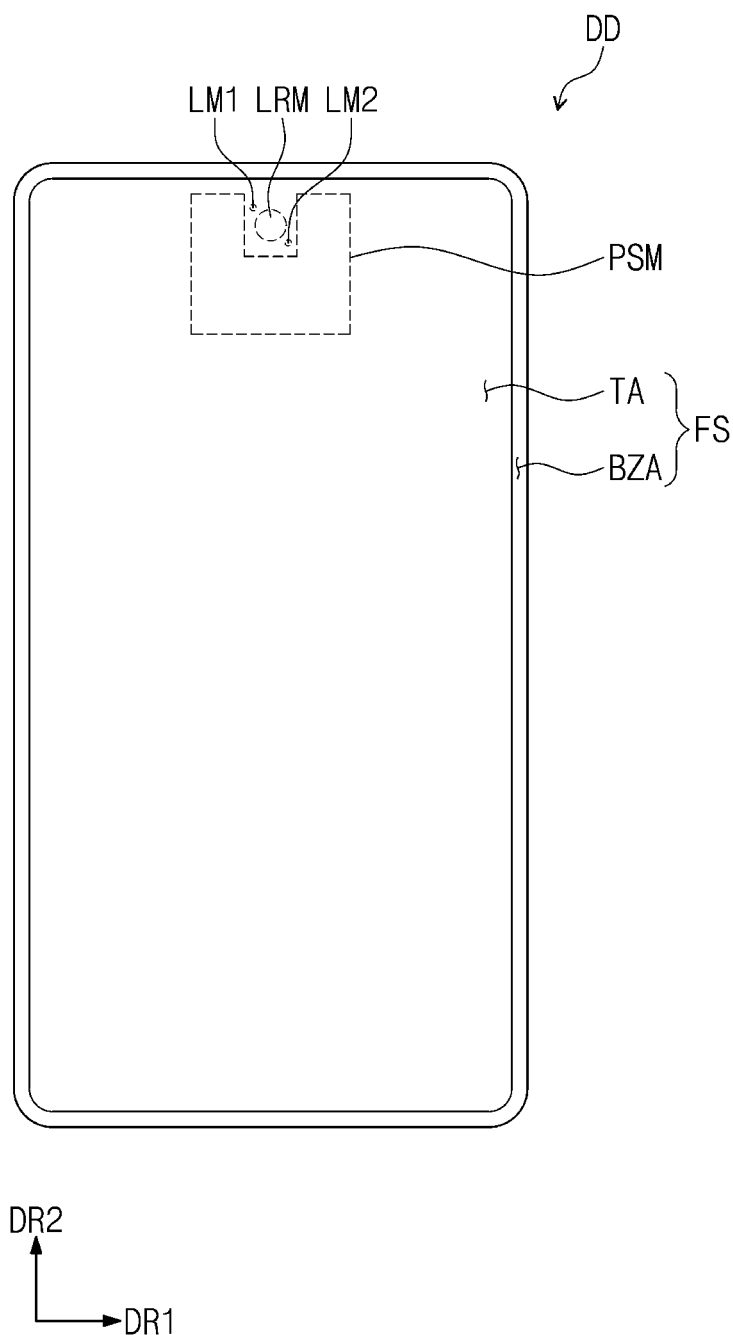
FIG. 9A is a plan view of an exemplary embodiment of a pressure sensing module, first and second light emitting modules, and a light receiving module in a display device constructed according to principles of the invention.
Figure 9B:
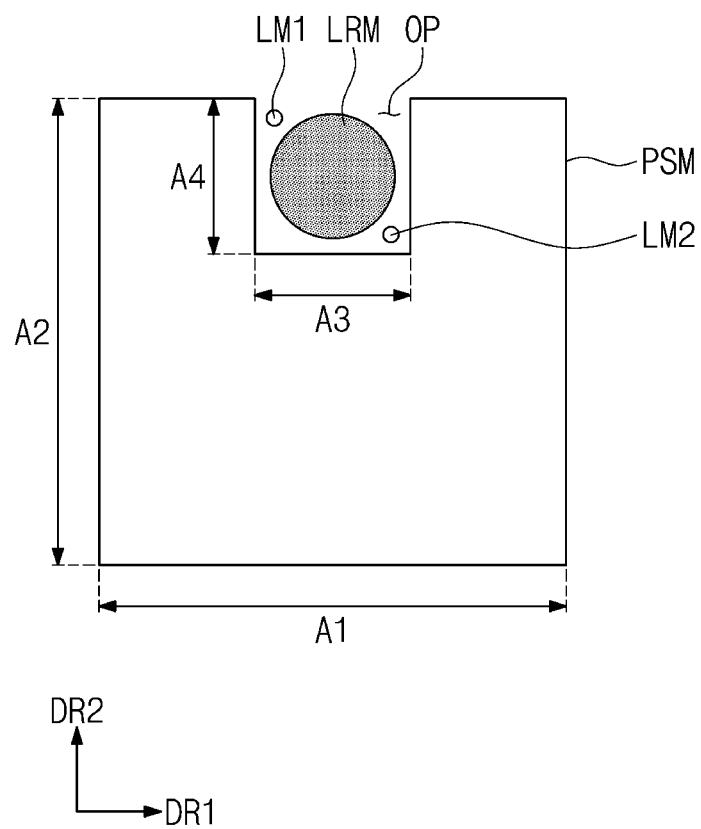
FIG. 9B is an enlarged view of the pressure sensing module, the first and second light emitting modules, and the light receiving module of FIG. 9A.

FIG. 9A is a plan view of an exemplary embodiment of a pressure sensing module, first and second light emitting modules, and a light receiving module in a display device constructed according to principles of the invention. FIG. 9B is an enlarged view of the pressure sensing module, the first and second light emitting modules, and the light receiving module of FIG. 9A.

FIG. 9A shows the position, in a plan view, of the pressure sensing module PSM, the first and second light emitting modules LM1 and LM2, and the light receiving module LRM in the display device DD according to some exemplary embodiments. FIG. 9B is an enlarged view of the pressure sensing module PSM, the first and second light emitting modules LM1 and LM2, and the light receiving module LRM illustrated in FIG. 9A.

With reference to FIGS. 9A and 9B, the pressure sensing module PSM has a generally U shape enclosing a portion of the first and second light emitting modules LM1 and LM2 and the light receiving module LRM. The shape of the pressure sensing module PSM is not limited to the example shown in FIG. 10, and may be variously changed. For example, the pressure sensing module PSM may have a generally closed curve shape (e.g., a generally annular shape or a generally circular ring shape) continuously connected along the circumference of the first and second light emitting modules LM1 and LM2 and the light receiving module LRM. The pressure sensing module PSM may be variously designed according to the shapes of the first and second light emitting modules LM1 and LM2, and the light receiving module LRM.

The first and second light emitting modules LM1 and LM2, and the light receiving module LRM overlap the second area DA2 of the display panel DP in a plan view. When the first area DA1 has a first light transmissivity, the second area DA2 may have a second light transmissivity higher than the first light transmissivity. Accordingly, light output from the first and second light emitting modules LM1 and LM2 may be delivered well to the outside (for example, a finger of the user) of the display device DD. In addition, light reflected from the outside (for example, a finger of the user) may be delivered well to the light receiving module LRM.

The pressure sensing module PSM has a first length A1 in the first direction DR1, and a second length A2 in the second direction DR2. The first length A1 and the second length A2 may be the same or different from each other. The first length A1 and the second length A2 may be defined to have sizes through which contact pressure of the user's finger may be sensed. For example, each of the first length A1 and the second length A2 may be about 20 mm.

An opening unit OP of the pressure sensing module PSM, in which the first and second light emitting modules LM1 and LM2, and the light receiving module LRM are disposed, has a third length A3 in the first direction DR1, and has a fourth length A4 in the second direction DR2. The third length A3 and the fourth length A4 may be the same or different from each other. The third length A3 and the fourth length A4 may be determined according to the sizes of the first and second light emitting modules LM1 and LM2, and the light receiving module LRM. For example, each of the third length A3 and the fourth length A4 may be about 5 mm.

Figure 10:
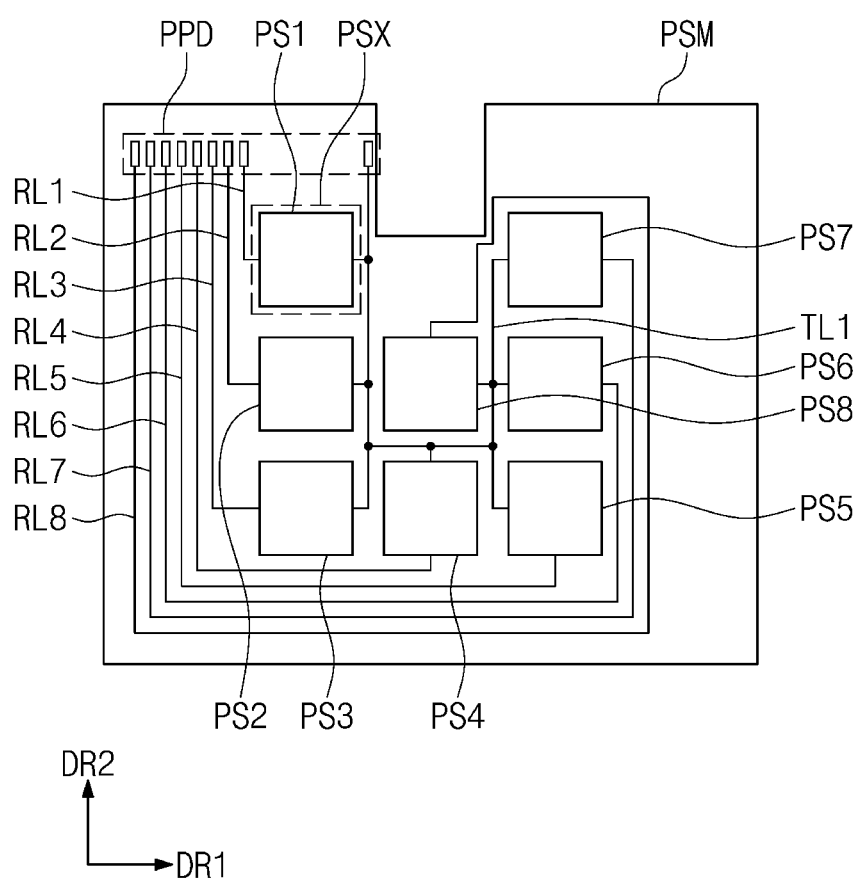
FIG. 10 is a plan view of an exemplary embodiment of a pressure sensing module constructed according to principles of the invention.

FIG. 10 is a plan view of an exemplary embodiment of a pressure sensing module constructed according to principles of the invention.

With reference to FIG. 10, the pressure sensing module PSM includes individual pressure sensor units PS1 to PS8, receiving lines RL1 to RL8, a transmission line TL1, and pads PPD. The receiving lines RL1 to RL8 may be respectively connected to the pressure sensor units PS1 to PS8, and the transmission line TL1 is commonly connected to the pressure sensor units PS1 to PS8. The pads PPD are respectively connected to the receiving lines RL1 to RL8 and the transmission line TL1. The pads PPD may be electrically connected to the main circuit board MB illustrated in FIG. 1B. For example, the display device DD (see FIG. 1B) may further include a circuit board for electrically connecting the pads PPD of the pressure sensing module PSM with the main circuit board MB.

Each of the pressure sensor units PS1 to PS8 may include a pressure sensitive material having characteristics that vary according to the magnitude of the applied pressure. In some exemplary embodiments, the pressure sensitive material may be metal nanoparticles, and the metal nanoparticles may be included in polymer.

Each of the pressure sensor units PS1 to PS8 receives a transmission signal through the transmission line TL1, and outputs, to the receiving lines RL1 to RL8, a sensing signal according to whether there is the contact pressure of the user. The pressure sensing module PSM illustrated in FIG. 10 includes eight pressure sensor units PS1 to PS8, but the exemplary embodiments are not limited thereto. The number and the type of the pressure sensor units may be variously changed.

Figure 11:
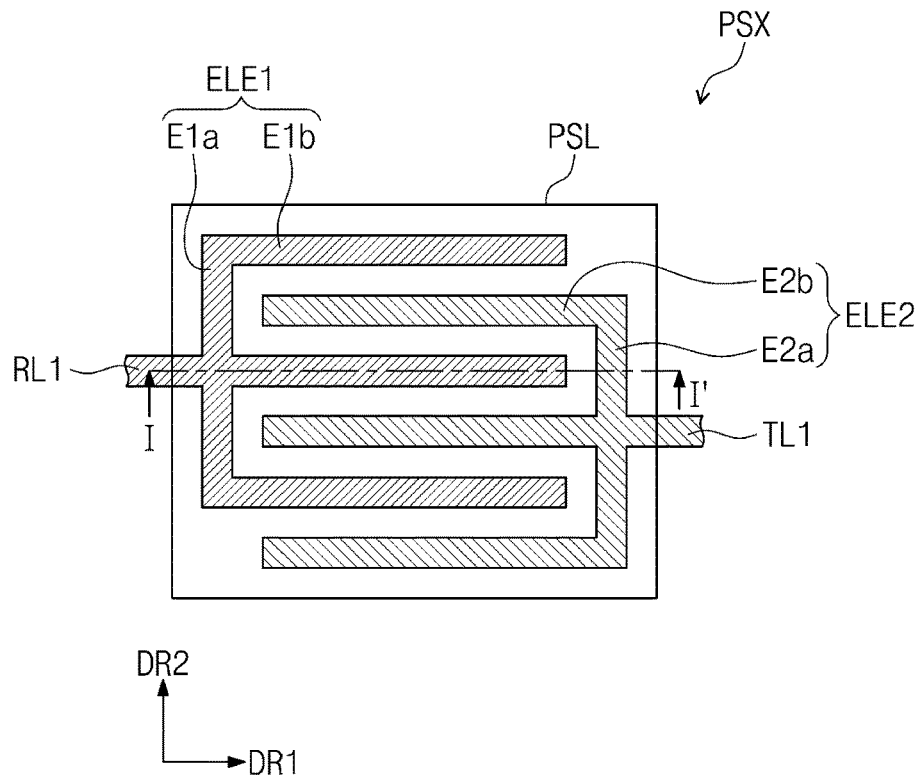
FIG. 11 is a plan view an exemplary embodiment of a pressure sensing region including a pressure sensor unit of FIG. 10.
Figure 12:
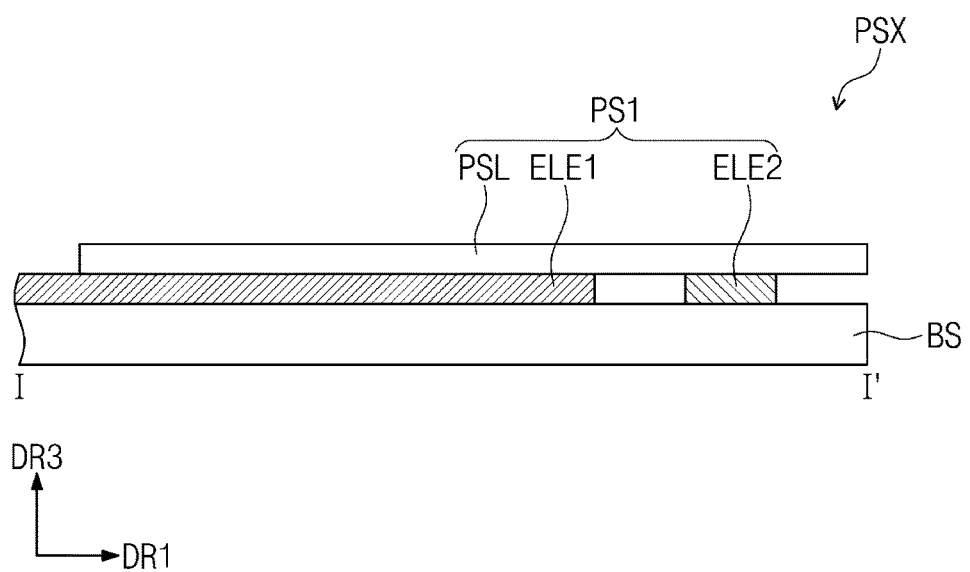
FIG. 12 is a cross-sectional view taken along line I-I' of FIG. 11.

FIG. 11 is a plan view an exemplary embodiment of an area including a pressure sensor unit of FIG. 10. FIG. 12 is a cross-sectional view taken along line I-I' of FIG. 11.

FIGS. 11 and 12 illustrate only the pressure sensor unit PS1, but the other pressure sensor units PS2 to PS8 may include substantially the same structure as the pressure sensor unit PS1. With reference to FIGS. 11 and 12, the pressure sensor unit PS1 is disposed on the base substrate BS. The pressure sensor unit PS1 includes a first electrode ELE1, a second electrode ELE2, and a pressure sensing layer PSL.

The first electrode ELE1 and the second electrode ELE2 are formed on the base substrate BS. The first electrode ELE1 and the second electrode ELE2 are spaced apart from each other. In some exemplary embodiments, an insulation layer may be disposed between the first electrode ELE1 and the second electrode ELE2. In other words, the first electrode ELE1 and the second electrode ELE2 may be formed by disposing the insulation layer on the base substrate B S, etching the insulation layer, and then forming a conductive layer.

The first electrode ELE1 includes a first body unit E1a and a first branch unit E1b. The first branch unit E1b extends from the first body unit E1a in the first direction DR1. The first electrode ELE1 may include two or more first branch units E1b. The first body unit E1a of the first electrode ELE1 is connected to the receiving line RL1.

The second electrode ELE2 includes a second body unit E2a and a second branch unit E2b. The second branch unit E2b extends from the second body unit E2a in the opposite direction to the first direction DR1. The second electrode ELE2 may include two or more second branch units E2b. The second body unit E2a of the second electrode ELE2 is connected to the transmission line TL1.

The first branch units E1b of the first electrode ELE1 and the second branch units E2b of the second electrode ELE2 may be alternately disposed in the second direction DR2 to have a comb type. The pressure sensitivity of the pressure sensor unit PS1 may be enhanced by the first branch units E1b of the first electrode ELE1 and the second branch units E2b of the second electrode ELE2, which have the comb type.

The first electrode ELE1 and the second electrode ELE2 may be formed from a transparent conductive material such as an indium tin oxide (ITO), or be formed of a low resistance metal material, for example, one or more materials selected from the group consisting of molybdenum (Mo), silver (Ag), titanium (Ti), copper (Cu), aluminum (Al), and a combination thereof. The first electrode ELE1 and the second electrode ELE2 are disposed on the same layer. In addition, the first electrode ELE1 and the second electrode ELE2 may be disposed on the same layer with the same material as the receiving lines RL1 to RL8 and the transmission line TL1 illustrated in FIG. 10. However, the exemplary embodiments are not limited thereto, and the first electrode ELE1 and the second electrode ELE2 may be disposed on a different layer from the receiving lines RL1 to RL8 and the transmission line TL1.

The pressure sensing layer PSL is disposed on the top portions of the first electrode ELE1 and the second electrode ELE2. The pressure sensing layer PSL may be directly disposed on the top portions of the first electrode ELE1 and the second electrode ELE2 to be electrically connected to each of the first electrode ELE1 and the second electrode ELE2. The pressure sensing layer PSL may include a pressure sensitive material responding to an external pressure.

In FIG. 11, the pressure sensing layer PSL is illustrated as having a generally rectangular shape, but the exemplary embodiments are not limited thereto. The shape of the pressure sensing layer PSL may be variously implemented to have a generally polygonal shape such as a generally diamond, a generally triangular, or a generally hexagonal, or a generally circular or a generally elliptical shape.

When contact pressure is applied by the user, the pressure sensing layer PSL may deliver a TX signal received through the transmission line TL1 to the receiving line RL1. The receiving line RL1 provides an RX signal received from the pressure sensing layer PSL to the pads PPD as depicted in FIG. 10.

Figure 13:
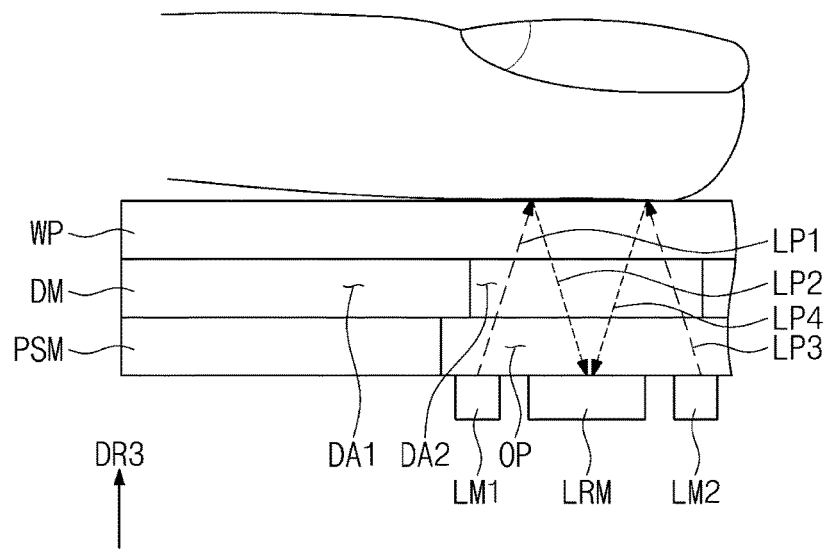
FIG. 13 is a schematic diagram depicting an exemplary embodiment of a blood pressure measurement operation of a light emitting module and a light receiving module according to principles of the invention.

FIG. 13 is a schematic diagram depicting an exemplary embodiment of a blood pressure measurement operation of a light emitting module and a light receiving module according to principles of the invention.

With reference to FIG. 13, light emitted from the first light emitting module LM1 reaches a finger of the user via a first light path LP1 through the opening unit OP of the pressure sensing module PSM and the second area DA2 of the display module DM. The light reaching the finger of the user may be reflected on a second light path LP2 to be delivered to the light receiving module LRM. In addition, the light emitted from the second light emitting module LM2 reaches the finger of the user via a third light path LP3, and then is reflected. The light reflected by the finger of the user may be delivered to the light receiving module LRM.

The first and second light emitting modules LM1 and LM2 output light to the fingers of the user, and the light receiving module LRM may receive the reflected light to measure the photoplethysmography. The photoplethysmography measurement measures, by means of light, a characteristic change in a reflection ratio, an absorption ratio, a transmissivity, or the like, with respect to a biometric tissue. The characteristic change is generated when the volume of a blood vessel changes. Accordingly, the light receiving module LRM may output a light sensing signal corresponding to the pulse wave of the user.

Figure 14:
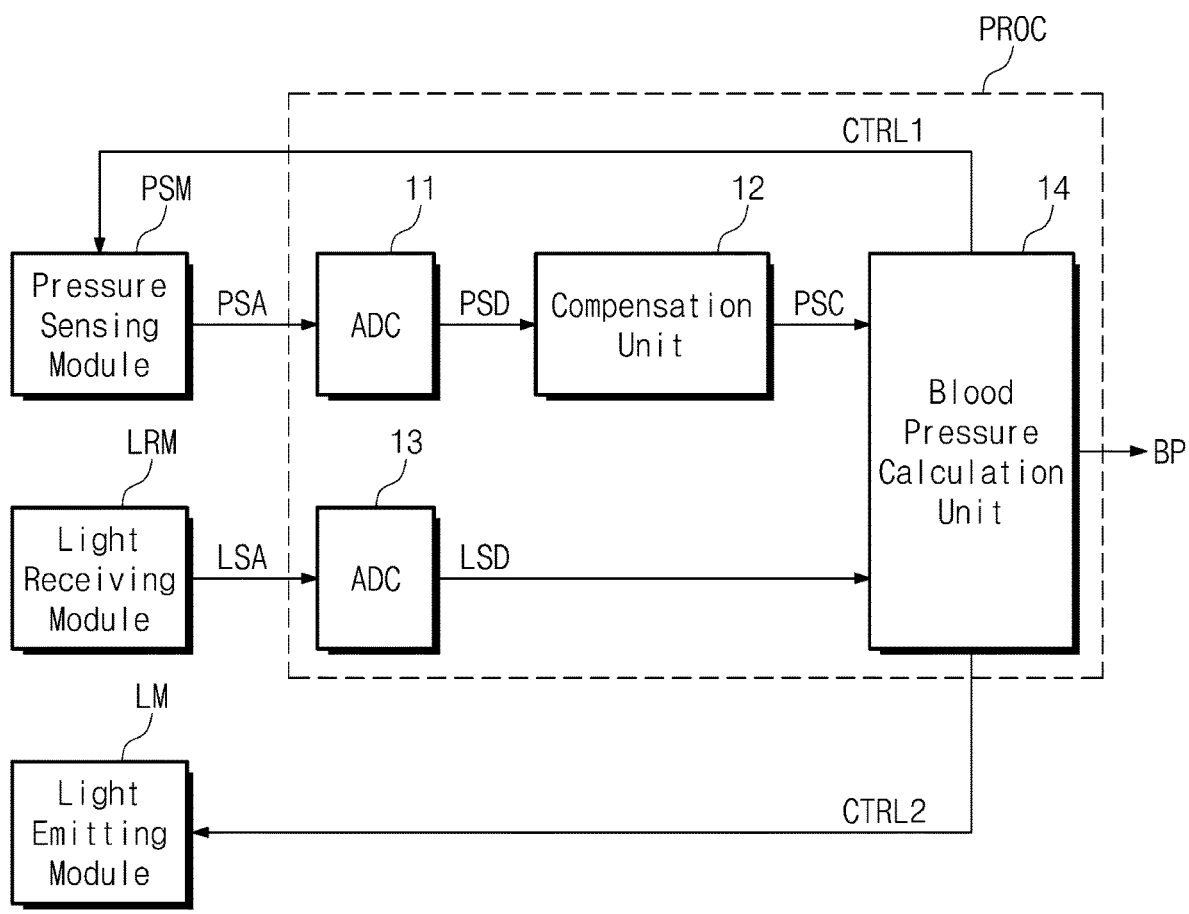
FIG. 14 is a block diagram of an exemplary embodiment for measuring blood pressure in a display device according to principles of the invention.

FIG. 14 is a block diagram of an exemplary embodiment for measuring blood pressure in a display device according to principles of the invention.

With reference to FIG. 14, the configuration for measuring the blood pressure, the display device DD includes a pressure sensing module PSM, a light receiving module LRM, a light emitting module LM, and a processor PROC. The light emitting module LM may include the first and second light emitting modules LM1 and LM2 illustrated in FIG. 1B. The processor PROC includes analog-to-digital converters 11 and 13, a compensation unit 12 and a blood pressure calculation unit 14. With reference to FIGS. 10 and 14, the processor PROC outputs a first control signal CTRL1 to the pressure sensing module PSM. The first control signal CTRL1 may be a TX signal. The first control signal CTRL1 is provided to the pressure sensor units PS1 to PS8 through the transmission line TL1. The pressure sensor units PS1 to PS8 sense the contact pressure of the user, and transmit the sensed signals to the pads PPD as an RX signal through the receiving lines RL1 to RL8. The RX signal from the pressure sensor units PS1 to PS8 may be provided to the analog-to-digital converter 11 in the processor PROC as a pressure sensing signal PSA. The pressure sensing signal PSA may be an analog voltage signal or an analog current signal. The analog-to-digital converter 11 converts the pressure sensing signal PSA received from the pressure sensing module PSM to a digital signal to output a digital pressure sensing signal PSD. The digital pressure sensing signal PSD may be provided to the compensation unit 12. The compensation unit 12 outputs a pressure-compensated signal PSC in which the digital pressure sensing signal PSD is compensated.

Figure 15:
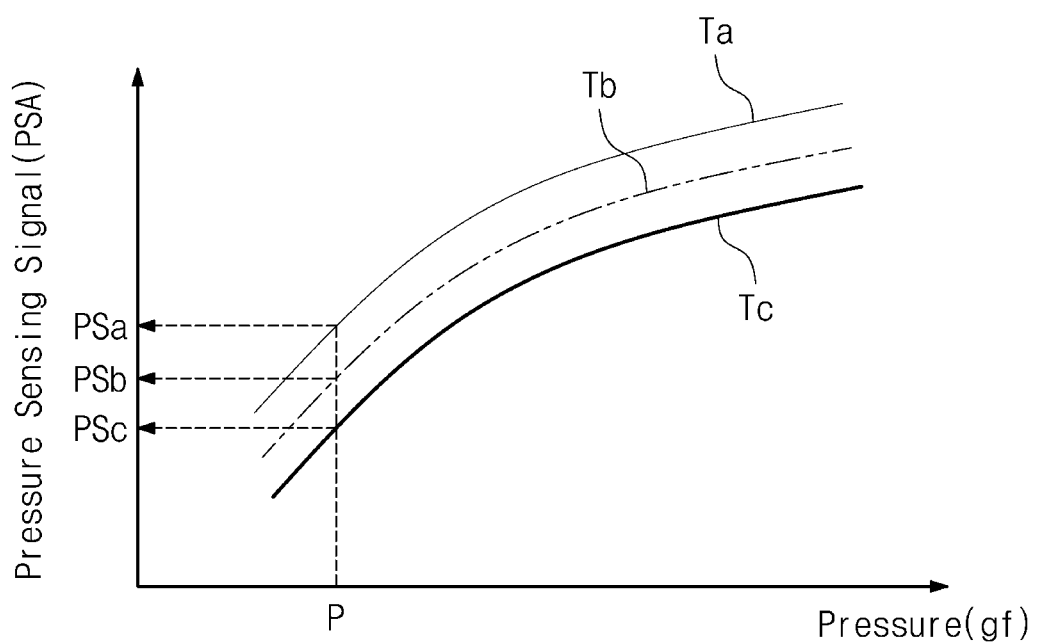
FIG. 15 is a graphical depiction explaining the operation of an exemplary embodiment of a compensation unit of FIG. 14.

FIG. 15 is a graphical depiction explaining the operation of an exemplary embodiment of a compensation unit of FIG. 14.

In FIG. 15, the curves Ta, Tb, and Tc depict an exemplarily pressure sensing signal PSA according to a contact area of the user. Here, the curves Ta, Tb, and Tc respectively correspond to the contact areas A, B, and C of the user. The contact areas have the relationship of A>B>C.

Even when the same pressure P is applied by the user's touch, the level of the pressure sensing signal PSA may become different as PSa, PSb, and PSc according to the contact area. The levels of the pressure sensing signal PSA have the relationship of PSa>PSb>PSc. In other words, as the contact area is larger for the same pressure P, the pressure sensing signal PSA have a higher level.

The compensation unit 12 shown in FIG. 14 may calculate the contact area of the user on the basis of the digital pressure sensing signal PSD, and output the pressure-compensated signal PSC in which the digital pressure sensing signal PSD is compensated in consideration of the calculated contact area. For example, when all the pressure sensor units PS1 to PS8 illustrated in FIG. 10 sense the pressure of the user (when the contact area is larger than a first reference value), the digital pressure sensing signal PSD may be reduced by a prescribed ratio. On the contrary, when the prescribed number or less of the pressure sensor units PS1 to PS8 (for example, 4 or fewer) illustrated in FIG. 10 sense the pressure of the user (when the contact area is larger than a second reference value), the digital pressure sensing signal PSD may be increased by a prescribed ratio. According to such an operation of the compensation unit 12, the blood pressure calculation unit 14 may calculate (measure or estimate) more accurately the blood pressure of the user.

The blood pressure calculation unit 14 outputs a second control signal CTRL2 to the light emitting module LM. The second control signal CTRL2 may be a signal for controlling the light emission operation of the light emitting module LM. The light output from the light emitting module LM may be reflected by the hand of the user and received by the light receiving module RLM. The light receiving module LRM may provide a light sensing signal LSA, which is an analog voltage signal or an analog current signal corresponding to the received light, to the processor PROC. The analog-to-digital converter 13 converts the light sensing signal LSA received from the light receiving module LRM to a digital light sensing signal LSD and outputs the digital light sensing signal LSD to the blood pressure calculation unit 14.

The blood pressure calculation unit 14 acquires information about the contact pressure on the basis of the pressure-compensated signal PSC, and acquires information about a pulse wave on the basis of the digital light sensing signal LSD. The blood pressure calculation unit 14 may analyze a change in the pulse wave according to the contact pressure to calculate the blood pressure of the user, and output a blood pressure signal BP corresponding to the calculate blood pressure.

The blood pressure may include a diastolic blood pressure (DBP), a systolic blood pressure (SBP), and a mean arterial pressure (MAP), and the contact pressure applied to the pressure sensing module by the user's finger may act as an external pressure applied to the blood vessel. When the contact pressure becomes smaller than the MAP, the elastic recovery force of tissues acts in a direction to compress the blood vessel and thus the amplitude of a pulse wave signal become smaller. When the contact pressure is equal to the MAP, the elastic recovery force of tissues becomes zero, the contact pressure does not act on the blood vessel, and thus the amplitude of the pulse wave signal becomes maximized. In addition, when the contact pressure becomes larger than the MAP, the elastic recovery force of tissues acts in a direction to expand the blood vessel, and thus the amplitude of the pulse wave signal becomes small. Accordingly, the blood pressure calculation unit 14 may analyze a change in the pulse wave signal according to the contact pressure, and estimate the contact pressure as the MAP when the amplitude of the pulse wave signal is the maximum. In addition, the blood pressure calculation unit 14 may calculate the contact pressure as the SBP at a point at which the amplitude has a first ratio (for example, about 0.7) of the maximum amplitude, and calculate the contact pressure as the DBP at a point at which the amplitude has a second ratio (for example, about 0.55) of the maximum amplitude.

The blood pressure calculation unit 14 senses a change in the light sensing level of the digital light sensing signal LSD, while the contact pressure of the user gradually increases and thus the pressure sensing level of the pressure-compensated signal PSC increases. The blood pressure calculation unit 14 estimates, as the MAP, the pressure sensing level of the pressure-compensated signal PSC corresponding to the point at which the light sensing level of the digital light sensing signal LSD is the maximum (the maximum light sensing level).

The blood pressure calculation unit 14 calculates, as the SBP, the pressure sensing level of the pressure-compensated signal PSC corresponding to the first ratio of the maximum light sensing level of the digital light sensing signal LSD corresponding to the MAP. The blood pressure calculation unit 14 calculates, as the DBP, the pressure sensing level of the pressure-compensated signal PSC corresponding to the second ratio of the maximum light sensing level of the digital light sensing signal LSD corresponding to the MAP. The blood pressure calculation unit 14 outputs the blood pressure signals BP corresponding to the SBP and the DBP.

Figure 16:
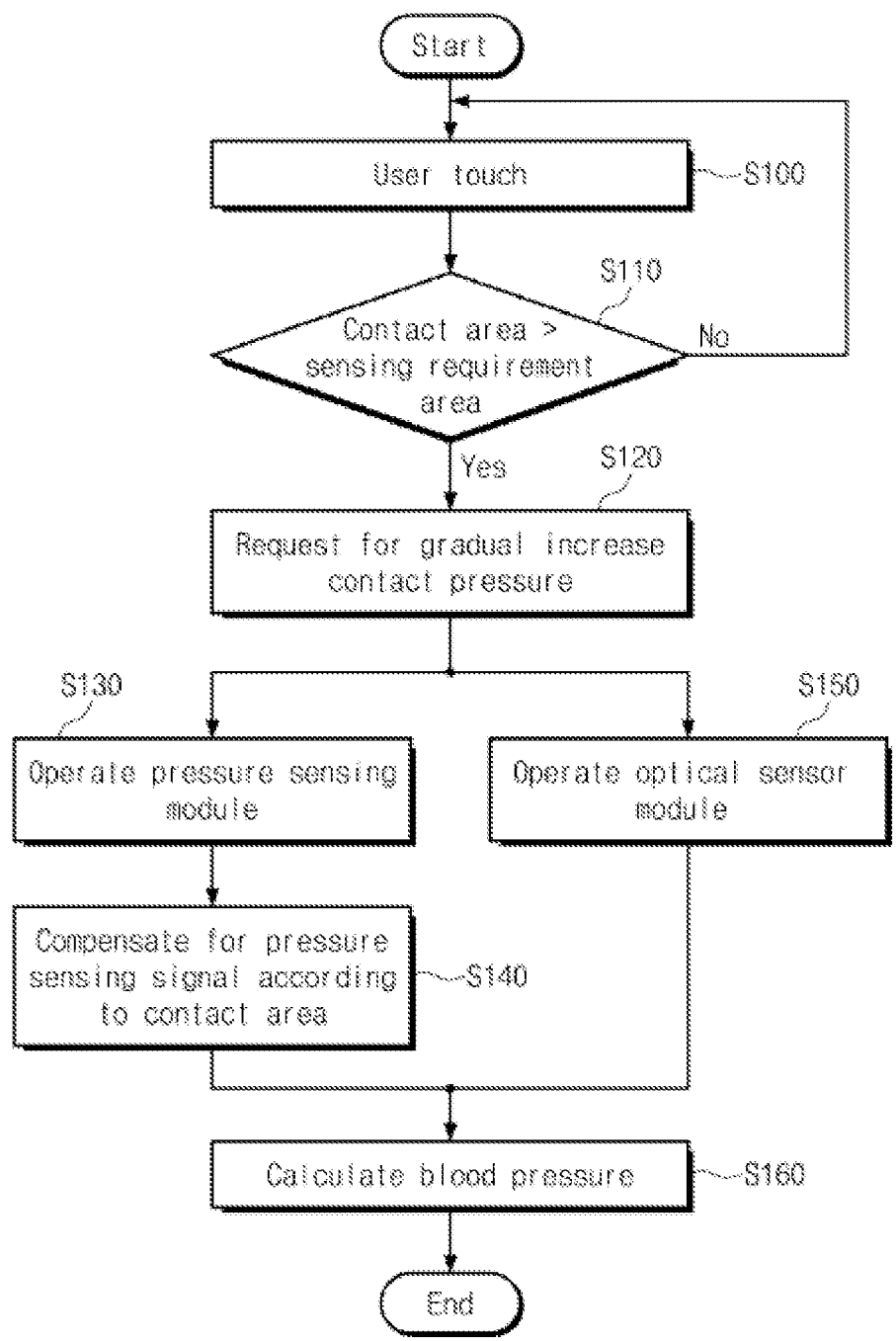
FIG. 16 is a flowchart illustrating an exemplary embodiment of a blood pressure measurement method of a display device according to principles of the invention.

FIG. 16 is a flowchart illustrating an exemplary embodiment of a blood pressure measurement method of a display device according to principles of the invention. For convenience of explanation, the blood pressure measurement method according to the embodiment will be described with reference to the display device illustrated in FIG. 14.

With reference to FIGS. 14 and 16, during a blood pressure measurement mode, the blood pressure calculation unit 14 senses a user's touch by transmitting the first control signal CTRL1 to the pressure sensing module PSM (step S100).

The blood pressure calculation unit 14 determines whether the contact area of the user is larger than a sensing requirement area on the basis of the pressure-compensated signal PSC received through the pressure sensing module PSM, the analog-to-digital converter 11 and the compensation unit 12 (step S110). For example, the prescribed number (e.g., 4) or greater of the pressure sensor units PS1 to PS8 illustrated in FIG. 10 transmit RX signals that indicate sensing of the pressure, the blood pressure calculation unit 14 may determine that the contact area of the user is larger than the sensing requirement area. When the contact area of the user is smaller than the sensing requirement area, the blood pressure calculation unit 14 outputs a message to the user to re-touch the finger to the pressure sensing module PSM, and senses again the user's touch. The blood pressure calculation unit 14 outputs a message requesting the magnitude of the contact pressure of the user to be gradually increased through the display module DM and/or a speaker (step S120).

As described above, the blood pressure calculation unit 14 may analyze a change in the pulse wave signal according to the contact pressure, and estimate the contact pressure as the MAP when the amplitude of the pulse wave signal is the maximum. In addition, the blood pressure calculation unit 14 may calculate the contact pressure as the SBP at a point at which the amplitude has the first ratio (for example, about 0.7) of the maximum amplitude, and calculate the contact pressure as the DBP at a point at which the amplitude has the second ratio (for example, about 0.55) of the maximum amplitude. Accordingly, the user is required to adjust gradually but firmly increase the magnitude of the contact pressure in the blood pressure measurement mode.

Figure 17:
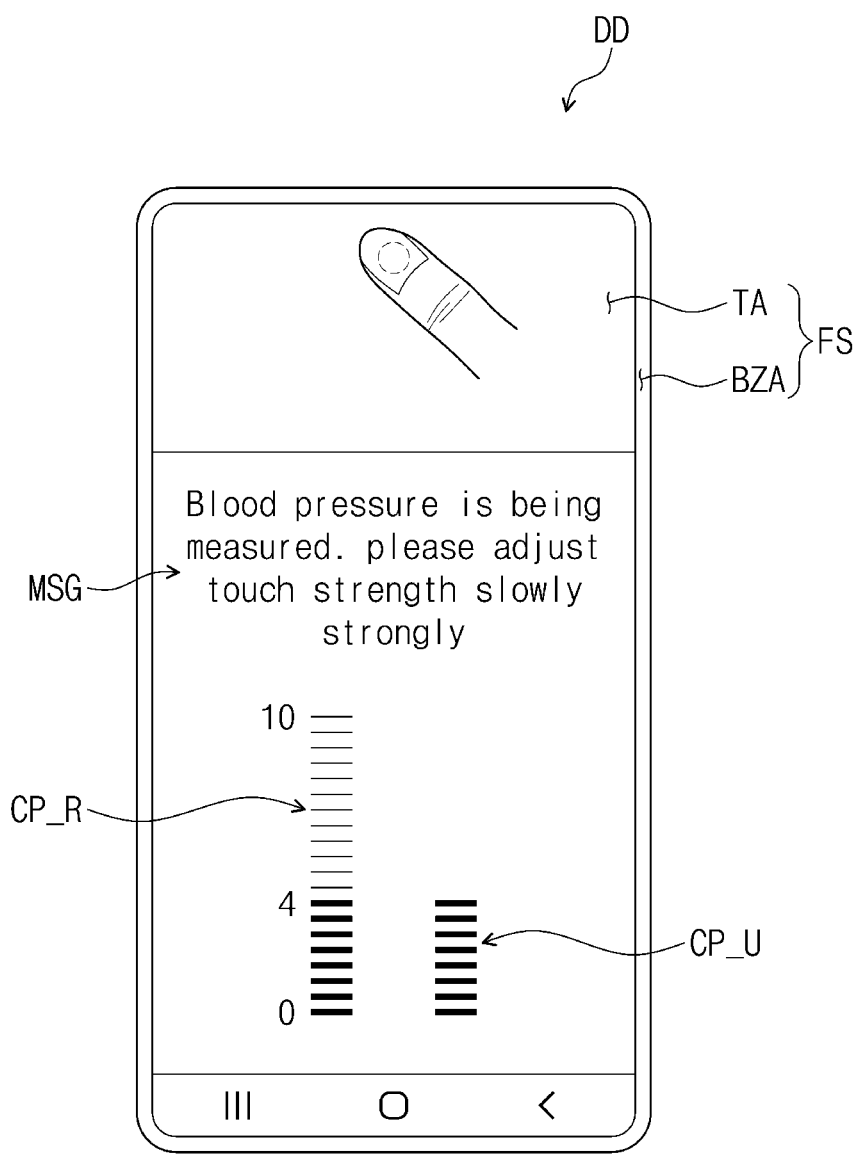
FIG. 17 is a plan view of an exemplary embodiment of a display device having a screen constructed according to principles of the invention for displaying a blood pressure measurement mode.

FIG. 17 is a plan view of an exemplary embodiment of a display device having a screen constructed according to principles of the invention for displaying a blood pressure measurement mode.

With reference to FIG. 17, the blood pressure calculation unit 14 outputs, on the display surface FS, a message MSG requesting the magnitude of the contact pressure of the user to be gradually increased and a reference graph CP_R showing a reference value of the contact pressure. The reference graph CP_R displays the magnitude of the contact pressure from level 0 to level 10. For example, when, in the blood pressure measurement mode, the contact pressure of the user is required to be maintained for a prescribed time (e.g., about 20 seconds) and the magnitude of the contact pressure is required to be changed from level 0 to level 10, the reference graph CP_R, which shows that the magnitude of the contact pressure varies from level 0 to level 10, may be displayed to the user for the prescribed time that the magnitude of the contact pressure is required to be changed. A user graph CP_U shows the magnitude of the contact pressure of the user. Accordingly, the user may adjust the magnitude of the contact pressure while watching the reference graph CP_R and the user graph CP_U concurrently.

With reference FIGS. 14 and 16, the pressure sensing module PSM senses the contact pressure of the user, and provides the pressure sensing signal PSA to the processor PROC (step S130, i.e., operate pressure sensing module). The analog-to-digital converter 11 in the processor PROC converts the pressure sensing signal PSA to the digital pressure sensing signal PSD. The compensation unit 12 receives the digital pressure sensing signal PSD and performs compensation according to the contact area to output the pressure-compensated signal PSC (step S140).

The optical sensor module senses the pulse wave of the user (step S150). The optical sensor module may include the light emitting module LM and the light receiving module LRM. In detail, the blood pressure calculation unit 14 outputs the second control signal CTRL2 to the light emitting module LM to control so that the light emitting module LM operates. The light receiving module LRM receives the light that has been output from the light emitting module LM and then reflected by the finger of the user, and provides the light sensing signal LSA to the processor PROC.

The analog-to-digital converter 13 in the processor PROC converts the light sensing signal LSA to the digital light sensing signal LSD. The blood pressure calculation unit 14 in the processor PROC may output the blood pressure signal BP on the basis of the pressure-compensated signal PSC from the compensation unit 12 and the light sensing signal LSA (step S160, i.e., calculate blood pressure). In detail, the blood pressure calculation unit 14 in the processor PROC may calculate (estimate) the blood pressure of the user on the basis of the pressure-compensated signal PSC from the compensation unit 12 and the light sensing signal LSA, and output the blood pressure signal BP corresponding to the calculated blood pressure.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A display device comprising:
    a display panel including a first area having a first light transmissivity and a second area having a second light transmissivity higher than the first light transmissivity;
    a pressure sensor overlapping the first area;
    a light emitter overlapping the second area;
    a light receiver overlapping the second area and spaced from the light emitter; and
    a processor to control the light emitter and the pressure sensor, and to output a blood pressure signal on a basis of a pressure sensing signal from the pressure sensor and a light sensing signal from the light receiver.

2. The display device of claim 1, wherein the pressure sensor comprises a pressure sensing module including:
    pressure sensor units;
    a transmission line to deliver a transmission signal to the pressure sensor units; and
    receiving lines respectively corresponding to the pressure sensor units, to deliver received signals from the pressure sensor units as the pressure sensing signal.

3. The display device of claim 2, wherein at least some of the pressure sensor units comprise:
    a first electrode on a base substrate;
    a second electrode on the base substrate and separated from the first electrode; and
    a pressure sensing layer directly disposed on the first electrode and the second electrode.

4. The display device of claim 3, wherein the first electrode is electrically connected to a corresponding receiving line of the receiving lines, and the second electrode is electrically connected to the transmission line.

5. The display device of claim 3, wherein
    the first electrode comprises a first body unit and first branch units to extend from the first body unit in a first direction, and
    the second electrode comprises a second body unit and second branch units to extend from the second body unit in an opposite direction to the first direction,
    wherein the first branch units and the second branch units are alternately disposed in a second direction that intersects with the first direction.

6. The display device of claim 1, wherein the processor comprises:
    a first analog-to-digital converter to convert the pressure sensing signal to a digital pressure sensing signal;
    a compensation unit to calculate a contact area on a basis of the digital pressure sensing signal, and to output a pressure-compensated signal in which the digital pressure sensing signal is compensated according to the contact area;
    a second analog-to-digital converter to convert the light sensing signal to a digital light sensing signal; and
    a blood pressure calculation unit to output the blood pressure signal on a basis of the pressure-compensated signal and the digital light sensing signal.

7. The display device of claim 6, wherein the blood pressure calculation unit is configured to output a first control signal for the pressure sensor to sense a contact pressure of a user during a blood pressure measurement mode, and to output a second control signal for the light emitter to output light.

8. The display device of claim 6, wherein the blood pressure calculation unit is configured to output, to the display panel, a message for requesting a magnitude of a contact pressure of a user to be gradually increased during a blood pressure measurement mode.

9. The display device of claim 6, wherein the blood pressure calculation unit is configured to enter a blood pressure measurement mode, when the contact area is larger than a sensing requirement area.

10. The display device of claim 6, wherein the compensation unit is configured to: reduce the digital pressure sensing signal by a prescribed ratio, when the contact area is larger than a first reference value, and increase the digital pressure sensing signal by a prescribed ratio, when the contact area is smaller than a second reference value.

11. The display device of claim 6, wherein the blood pressure calculation unit is configured to sense a change in a light sensing level of the digital light sensing signal, while a contact pressure of a user gradually increases and thus a pressure sensing level of the pressure-compensated signal increases.

12. The display device of claim 11, wherein the blood pressure calculation unit is configured to:
    calculate the pressure sensing level, which corresponds to a point at which the light sensing level is a maximum, as a mean arterial pressure;
    calculate the pressure sensing level of the pressure-compensated signal, which corresponds to a first ratio of the light sensing level corresponding to the mean arterial pressure, as a systolic blood pressure;
    calculate the pressure sensing level, which corresponds to a second ratio of the light sensing level corresponding to the mean arterial pressure, as a diastolic blood pressure; and output the blood pressure signal corresponding to each of the systolic blood pressure and the diastolic blood pressure.

13. The display device of claim 1, wherein the light emitter comprises a first light emitting module and a second light emitting module separately disposed from each other.

14. The display device of claim 1, wherein the pressure sensor has a shape substantially enclosing at least a portion of the light emitter and the light receiver.

* * * * *